United States Patent
Mascarenhas

(10) Patent No.: US 12,102,685 B2
(45) Date of Patent: Oct. 1, 2024

(54) IMMODULATOR PEPTIDES COVALENTLY MODIFIED WITH SMALL MOLECULES

(71) Applicant: Desmond Mascarenhas, Auburn, CA (US)

(72) Inventor: Desmond Mascarenhas, Auburn, CA (US)

( * ) Notice: Subject to any disclaimer, the term of this patent is extended or adjusted under 35 U.S.C. 154(b) by 240 days.

(21) Appl. No.: 17/756,376

(22) PCT Filed: Mar. 26, 2020

(86) PCT No.: PCT/US2020/024828
§ 371 (c)(1),
(2) Date: May 24, 2022

(87) PCT Pub. No.: WO2021/194491
PCT Pub. Date: Sep. 30, 2021

(65) Prior Publication Data
US 2023/0020406 A1    Jan. 19, 2023

(51) Int. Cl.
| | |
|---|---|
| *A61K 38/17* | (2006.01) |
| *A61K 47/54* | (2017.01) |
| *A61P 37/02* | (2006.01) |
| *C07K 14/47* | (2006.01) |
| *G01N 33/50* | (2006.01) |

(52) U.S. Cl.
CPC ........ *A61K 47/542* (2017.08); *A61K 38/1754* (2013.01); *A61P 37/02* (2018.01); *C07K 14/4743* (2013.01); *G01N 33/5041* (2013.01); *G01N 2333/4745* (2013.01); *G01N 2510/00* (2013.01)

(58) Field of Classification Search
CPC .............. A61K 38/1754; A61K 47/542; C07K 14/4743; G01N 33/5041; G01N 2333/4745; G01N 2510/00
See application file for complete search history.

(56) References Cited

U.S. PATENT DOCUMENTS

| | | | | |
|---|---|---|---|---|
| 5,783,662 | A * | 7/1998 | Janmey | C07K 7/06 530/345 |
| 7,618,816 | B2 * | 11/2009 | Mascarenhas | C07K 14/4743 435/69.7 |
| 2003/0161829 | A1 * | 8/2003 | Mascarenhas | C07K 14/4743 514/251 |
| 2009/0053203 | A1 * | 2/2009 | Mascarenhas | A61P 25/00 514/762 |
| 2018/0078608 | A1 * | 3/2018 | Mascarenhas | G01N 33/6893 |

\* cited by examiner

*Primary Examiner* — Jeffrey E. Russel

(57) ABSTRACT

This invention provides modified IGFBP-derived peptides—collectively termed "immodulator peptides"—and related compositions and methods. Chemical modifications to peptides using small molecules, and sequence extensions to immodulator core sequences exhibit new and surprising biological activities. The invention builds the combinatorial power of the immodulator peptide class further by demonstrating which core sequences bind metal or glycosaminoglycans such as heparin. The invention discloses some surprising biological properties of compositions derived from these modifications, including a host of new therapeutic and diagnostic utilities (e.g. immune modulation of TLR signaling, enhanced collagen synthesis by skin fibroblasts, and synergy with a RIG-I agonist in killing melanoma cells). The invention also teaches methods for enhancing previously disclosed uses of immodulator peptides by showing how the modifications of the invention can boost the efficacy of immodulator peptides in a model of burn trauma.

7 Claims, No Drawings
Specification includes a Sequence Listing.

SEQUENCE LISTING

```
<160> NUMBER OF SEQ ID NOS: 32

<210> SEQ ID NO 1
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(20)
<223> OTHER INFORMATION: Xaa is any amino acid

<400> SEQUENCE: 1

Gly Xaa Phe Xaa Xaa Xaa Gln Cys Xaa Xaa Xaa Xaa Xaa Xaa Xaa
1               5                   10                  15

Gly Xaa Cys Trp
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(20)
<223> OTHER INFORMATION: Xaa is any amino acid

<400> SEQUENCE: 2

Gly Xaa Tyr Xaa Xaa Xaa Gln Cys Xaa Xaa Xaa Xaa Xaa Xaa Xaa
1               5                   10                  15

Gly Xaa Cys Trp
            20

<210> SEQ ID NO 3
<211> LENGTH: 20
<212> TYPE: PRT
```

```
<213> ORGANISM: Artificial Sequence
<220> FEATURE:
<223> OTHER INFORMATION: Synthetic

<400> SEQUENCE: 3

Gly Phe Tyr His Ser Arg Gln Cys Glu Thr Ser Met Asp Gly Glu Ala
1               5                   10                  15

Gly Leu Cys Trp
            20

<210> SEQ ID NO 4
<211> LENGTH: 20
<212> TYPE: PRT
<213> ORGANISM: Artificial Sequence
<220> FEATURE:
<223> OTHER INFORMATION: Synthetic

<400> SEQUENCE: 4

Gly Leu Tyr Asn Leu Lys Gln Cys Lys Met Ser Leu Asn Gly Gln Arg
1               5                   10                  15

Gly Glu Cys Trp
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic

<400> SEQUENCE: 5

Gly Phe Tyr Lys Lys Lys Gln Cys Arg Pro Ser Lys Gly Arg Lys Arg
1               5                   10                  15

Gly Phe Cys Trp
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic

<400> SEQUENCE: 6

Gly Asn Phe His Pro Lys Gln Cys His Pro Ala Leu Asp Gly Gln Arg
1               5                   10                  15

Gly Lys Cys Trp
            20

<210> SEQ ID NO 7
<211> LENGTH: 20
<212> TYPE: PRT
<213> ORGANISM: Artificial Sequence
<220> FEATURE:
<223> OTHER INFORMATION: Synthetic

<400> SEQUENCE: 7

Gly Phe Tyr Lys Arg Lys Gln Cys Lys Pro Ser Arg Gly Arg Lys Arg
1               5                   10                  15

Gly Ile Cys Trp
            20

<210> SEQ ID NO 8
<211> LENGTH: 20
```

```
<212> TYPE: PRT
<213> ORGANISM: Artificial Sequence
<220> FEATURE:
<223> OTHER INFORMATION: Synthetic

<400> SEQUENCE: 8

Gly Phe Tyr Arg Lys Arg Gln Cys Arg Ser Ser Gln Gly Gln Arg Arg
1               5                   10                  15

Gly Pro Cys Trp
            20

<210> SEQ ID NO 9
<211> LENGTH: 9
<212> TYPE: PRT
<213> ORGANISM: Artificial Sequence
<220> FEATURE:
<223> OTHER INFORMATION: Synthetic

<400> SEQUENCE: 9

Ala Phe Asn Ser Tyr Glu Leu Gly Ser
1               5

<210> SEQ ID NO 10
<211> LENGTH: 19
<212> TYPE: PRT
<213> ORGANISM: Artificial Sequence
<220> FEATURE:
<223> OTHER INFORMATION: Synthetic

<400> SEQUENCE: 10

Arg Gly Val Thr Glu Asp Tyr Leu Arg Leu Glu Thr Leu Val Gln Lys
1               5                   10                  15

Val Val Ser

<210> SEQ ID NO 11
<211> LENGTH: 19
<212> TYPE: PRT
<213> ORGANISM: Artificial Sequence
<220> FEATURE:
<223> OTHER INFORMATION: Synthetic

<400> SEQUENCE: 11

Thr Gly Pro Ser Glu Ser Tyr Leu Gln Leu Glu Glu Leu Val Lys Gln
1               5                   10                  15

Val Val Ser

<210> SEQ ID NO 12
<211> LENGTH: 9
<212> TYPE: PRT
<213> ORGANISM: Artificial Sequence
<220> FEATURE:
<223> OTHER INFORMATION: Synthetic

<400> SEQUENCE: 12

Ser Leu Asn Pro Glu Trp Asn Glu Thr
1               5

<210> SEQ ID NO 13
<211> LENGTH: 10
<212> TYPE: PRT
<213> ORGANISM: Artificial Sequence
<220> FEATURE:
<223> OTHER INFORMATION: Synthetic

<400> SEQUENCE: 13
```

Glu Thr Phe Ser Asp Val Trp Lys Leu Leu
1               5                  10

<210> SEQ ID NO 14
<211> LENGTH: 10
<212> TYPE: PRT
<213> ORGANISM: Artificial Sequence
<220> FEATURE:
<223> OTHER INFORMATION: Synthetic

<400> SEQUENCE: 14

Glu Thr Phe Ser Asp Ile Trp Lys Leu Leu
1               5                  10

<210> SEQ ID NO 15
<211> LENGTH: 22
<212> TYPE: PRT
<213> ORGANISM: Artificial Sequence
<220> FEATURE:
<223> OTHER INFORMATION: Synthetic

<400> SEQUENCE: 15

Lys Asn Gly Phe Tyr His Ser Arg Gln Cys Glu Thr Ser Met Asp Gly
1               5                   10                  15

Glu Ala Gly Leu Cys Trp
            20

<210> SEQ ID NO 16
<211> LENGTH: 22
<212> TYPE: PRT
<213> ORGANISM: Artificial Sequence
<220> FEATURE:
<223> OTHER INFORMATION: Synthetic

<400> SEQUENCE: 16

Lys His Gly Leu Tyr Asn Leu Lys Gln Cys Lys Met Ser Leu Asn Gly
1               5                   10                  15

Gln Arg Gly Glu Cys Trp
            20

<210> SEQ ID NO 17
<211> LENGTH: 22
<212> TYPE: PRT
<213> ORGANISM: Artificial Sequence
<220> FEATURE:
<223> OTHER INFORMATION: Synthetic

<400> SEQUENCE: 17

Lys Lys Gly Phe Tyr Lys Lys Gln Cys Arg Pro Ser Lys Gly Arg
1               5                   10                  15

Lys Arg Gly Phe Cys Trp
            20

<210> SEQ ID NO 18
<211> LENGTH: 22
<212> TYPE: PRT
<213> ORGANISM: Artificial Sequence
<220> FEATURE:
<223> OTHER INFORMATION: Synthetic

<400> SEQUENCE: 18

Arg Asn Gly Asn Phe His Pro Lys Gln Cys His Pro Ala Leu Asp Gly
1               5                   10                  15

Gln Arg Gly Lys Cys Trp
            20

<210> SEQ ID NO 19
<211> LENGTH: 22
<212> TYPE: PRT
<213> ORGANISM: Artificial Sequence
<220> FEATURE:
<223> OTHER INFORMATION: Synthetic

<400> SEQUENCE: 19

Arg Lys Gly Phe Tyr Lys Arg Lys Gln Cys Lys Pro Ser Arg Gly Arg
1               5                   10                  15

Lys Arg Gly Ile Cys Trp
            20

<210> SEQ ID NO 20
<211> LENGTH: 22
<212> TYPE: PRT
<213> ORGANISM: Artificial Sequence
<220> FEATURE:
<223> OTHER INFORMATION: Synthetic

<400> SEQUENCE: 20

His Arg Gly Phe Tyr Arg Lys Arg Gln Cys Arg Ser Ser Gln Gly Gln
1               5                   10                  15

Arg Arg Gly Pro Cys Trp
            20

<210> SEQ ID NO 21
<211> LENGTH: 40
<212> TYPE: PRT
<213> ORGANISM: Artificial Sequence
<220> FEATURE:
<223> OTHER INFORMATION: Synthetic

<400> SEQUENCE: 21

Arg Gly Val Thr Glu Asp Tyr Leu Arg Leu Glu Thr Leu Val Gln Lys
1               5                   10                  15

Val Val Ser Lys Gly Phe Tyr Lys Lys Lys Gln Cys Arg Pro Ser Lys
                20                  25                  30

Gly Arg Lys Arg Gly Phe Cys Trp
            35                  40

<210> SEQ ID NO 22
<211> LENGTH: 40
<212> TYPE: PRT
<213> ORGANISM: Artificial Sequence
<220> FEATURE:
<223> OTHER INFORMATION: Synthetic

<400> SEQUENCE: 22

Thr Gly Pro Ser Glu Ser Tyr Leu Gln Leu Glu Glu Leu Val Lys Gln
1               5                   10                  15

Val Val Ser Lys Gly Phe Tyr Lys Lys Lys Gln Cys Arg Pro Ser Lys
                20                  25                  30

Gly Arg Lys Arg Gly Phe Cys Trp
            35                  40

<210> SEQ ID NO 23
<211> LENGTH: 25
<212> TYPE: PRT
<213> ORGANISM: Artificial Sequence
<220> FEATURE:
<223> OTHER INFORMATION: Synthetic

```
<400> SEQUENCE: 23

Lys Lys Gly Phe Tyr Lys Lys Lys Gln Cys Arg Pro Ser Lys Gly Arg
1               5                   10                  15

Lys Arg Gly Phe Cys Trp Ala Val Asp
            20                  25

<210> SEQ ID NO 24

<400> SEQUENCE: 24

000

<210> SEQ ID NO 25
<211> LENGTH: 25
<212> TYPE: PRT
<213> ORGANISM: Artificial Sequence
<220> FEATURE:
<223> OTHER INFORMATION: Synthetic

<400> SEQUENCE: 25

Lys Lys Gly Phe Tyr Lys Lys Lys Gln Cys Arg Pro Ser Lys Gly Arg
1               5                   10                  15

Lys Arg Gly Phe Cys Trp Phe Val Ser
            20                  25

<210> SEQ ID NO 26
<211> LENGTH: 30
<212> TYPE: PRT
<213> ORGANISM: Artificial Sequence
<220> FEATURE:
<223> OTHER INFORMATION: Synthetic

<400> SEQUENCE: 26

Ser Leu Asn Pro Glu Trp Asn Glu Thr Lys Gly Phe Tyr Lys Lys Lys
1               5                   10                  15

Gln Cys Arg Pro Ser Lys Gly Arg Lys Arg Gly Phe Cys Trp
            20                  25                  30

<210> SEQ ID NO 27
<211> LENGTH: 31
<212> TYPE: PRT
<213> ORGANISM: Artificial Sequence
<220> FEATURE:
<223> OTHER INFORMATION: Synthetic

<400> SEQUENCE: 27

Ser Leu Asn Pro Glu Trp Asn Glu Thr Lys Lys Gly Phe Tyr Lys Lys
1               5                   10                  15

Lys Gln Cys Arg Pro Ser Lys Gly Arg Lys Arg Gly Phe Cys Trp
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: Synthetic

<400> SEQUENCE: 28

Ser Leu Asn Pro Glu Trp Asn Glu Thr His Gly Leu Tyr Asn Leu Lys
1               5                   10                  15

Gln Cys Lys Met Ser Leu Asn Gly Gln Arg Gly Glu Cys Trp
            20                  25                  30
```

```
<210> SEQ ID NO 29
<211> LENGTH: 30
<212> TYPE: PRT
<213> ORGANISM: Artificial Sequence
<220> FEATURE:
<223> OTHER INFORMATION: Synthetic

<400> SEQUENCE: 29

Ala Phe Asn Ser Tyr Glu Leu Gly Ser Lys Gly Phe Tyr Lys Lys Lys
1               5                   10                  15

Gln Cys Arg Pro Ser Lys Gly Arg Lys Arg Gly Phe Cys Trp
            20                  25                  30

<210> SEQ ID NO 30
<211> LENGTH: 31
<212> TYPE: PRT
<213> ORGANISM: Artificial Sequence
<220> FEATURE:
<223> OTHER INFORMATION: Synthetic

<400> SEQUENCE: 30

Ala Phe Asn Ser Tyr Glu Leu Gly Ser Lys Lys Gly Phe Tyr Lys Lys
1               5                   10                  15

Lys Gln Cys Arg Pro Ser Lys Gly Arg Lys Arg Gly Phe Cys Trp
            20                  25                  30

<210> SEQ ID NO 31
<211> LENGTH: 35
<212> TYPE: PRT
<213> ORGANISM: Artificial Sequence
<220> FEATURE:
<223> OTHER INFORMATION: Synthetic

<400> SEQUENCE: 31

Ala Phe Asn Ser Tyr Glu Leu Gly Ser Lys Gly Phe Tyr Lys Lys Lys
1               5                   10                  15

Gln Cys Arg Pro Ser Lys Gly Arg Lys Arg Gly Phe Cys Trp Ala Val
            20                  25                  30

Asp Lys Tyr
        35

<210> SEQ ID NO 32
<211> LENGTH: 31
<212> TYPE: PRT
<213> ORGANISM: Artificial Sequence
<220> FEATURE:
<223> OTHER INFORMATION: Synthetic

<400> SEQUENCE: 32

Phe Asn Ser Tyr Glu Leu Gly Ser Leu Lys Lys Gly Phe Tyr Lys Lys
1               5                   10                  15

Lys Gln Cys Arg Pro Ser Lys Gly Arg Lys Arg Gly Phe Cys Trp
            20                  25                  30
```

IMMODULATOR PEPTIDES COVALENTLY MODIFIED WITH SMALL MOLECULES

The entire contents of the Sequence Listing ASCII text file named 17756376_SeqList3.txt, created on May 26, 2024, and having a size of 9 KB, is incorporated by reference.

TECHNICAL FIELD

This invention relates to the field of peptide diagnostics and therapeutics, and more particularly to a combinatorial technology for expanding the class of IGFBP-derived peptides herein termed "immodulator peptides" by covalent and non-covalent modifications, thereby generating a wide array of compositions. Some of these compositions show surprising new or improved biological activities, suggesting their usefulness as pharmaceutical interventions for treating a wide range of symptoms of immune dysfunction or perturbation in mammals.

SUMMARY OF THE INVENTION

The present invention provides compositions and methods whereby a pharmaceutical composition containing a substantially purified ~20-60 amino-acid-long synthetic peptide, comprising an IGFBP-derived "immodulator" core sequence and at least one of several specified modifications to its composition, is administered to a mammal showing symptoms of immune dysfunction or perturbation, thereby ameliorating said symptoms. The technical problems addressed by this invention include the limited potencies and known range of of efficacies of previously disclosed immodulator sequences, the limited scope of targeting, binding and cell modulation displayed by previously disclosed compositions, limitations such as solubility and bioavailability of small molecules and metal complexes, and industrial considerations such as cost of goods and regulatory issues.

This invention describes new compositions wherein immodulator peptides are chemically modified at their amino terminus by the covalent addition of a small molecule, a carboxylic acid that is not a proteinogenic amino acid or biotin. This invention shows, for the first time, that ~20-60 amino-acid-long synthetic peptides containing different immodulator core sequences have different biologically-relevant activities.

The shortage of new drug candidates represents a severe crisis in modern drug development. The reasons that have led to the current crisis include the exploding costs associated with drug development, industry consolidation, gross inefficiencies at the interface of laboratory science and industrial development and, most of all, the increasingly stringent safety requirements imposed by regulatory agencies and informed consumers, which have continually raised the bar on safety testing, leading to many more failed drug candidates. Most major pharmaceutical companies would welcome a combinatorial technology platform to help solve these challenges and this invention creates such a platform. Peptide drugs combine the best features of "old" small-molecule drugs (cost of production, storage stability) with the best of modern biopharmaceutical drugs (biological specificity, natural design) and already account for over a quarter of market share in diabetes, one of the largest and fastest-growing market segments in the industry. As a technology platform, the immodulator peptide compositions of this invention provide for the combinatorial power of multiple immodulator core sequences, potentially hundreds of covalently attached N-terminal small molecules, and a range of binary complexes incorporating peptide-binding partners selected from metals, metallocenes and glycosaminoglycans.

Modern drug development frequently requires co-development of diagnostic tools for selecting patients and tracking drug efficacy. Accordingly, this invention provides new methods for biological potency measurements of immodulator peptides in purified form and in body fluids.

Small changes in the physical structure of immodulator peptides can simultaneously address multiple technical problems at once. For example, N-terminal covalent linkage of an immodulator peptide to certain therapeutic small molecules described in this invention can slow the rate of biological degradation of the peptide itself, improve the aqueous solubility and bioavailability of an otherwise insoluble small molecule, alter the preferred route of uptake (e.g. lymphatic versus portal, a matter of significance to disease conditions such as metastatic cancer) and target intra-organ tissues and cell types preferentially (an option not previously available for the small molecule in question), beneficially modulate the therapeutic efficacy or safety of the peptide in disease contexts, alter the range of binary complexes that a peptide can form, and aid in the manufacture of the peptide in industrial production settings.

Immunogenicity concerns may sometimes arise in cases of extended treatment with peptide pharmaceuticals. Immodulator peptides are based on natural human sequences, and nearly all of the sequence extensions disclosed in the current invention are natural human sequences. Peptides consisting solely of natural human sequences are intrinsically less likely to provoke immunogenicity concerns. This is yet another beneficial aspect of the technology.

The peptides of this invention are new based on their terminal modification with a member of a defined class of small molecules containing a free carboxyl group (instantiated hereunder with >25 different molecules); an extended range of immodulator core sequences provided as scaffolds; metal/metallocene- and glycosaminoglycan-peptide complexes; and peptide sequence extensions that confer new utilities to immodulator peptides.

|  | IGFBP-derived core SEQ ID NO: | | | | | |
| --- | --- | --- | --- | --- | --- | --- |
|  | 3 | 4 | 5 | 6 | 7 | 8 |
| covalent linkage to small molecule class | No | No | No | No | No | No |
| core sequence used as peptide scaffold | No | No | Yes | No | No | No |
| core extended by SEQ ID NOs: 15-22 # | No | No | No | No | No | No |
| core extended by SEQ ID NOs: 10-14 * | No | No | Yes | No | No | No |
| purified peptide complexes with metals # | No | No | No | No | No | No |
| peptide binding to glycosaminoglycan # | No | No | No | No | No | No |
| improved potencies on old utilities # | No | No | No | No | No | No |

-continued

|  | IGFBP-derived core SEQ ID NO: | | | | | |
|---|---|---|---|---|---|---|
|  | 3 | 4 | 5 | 6 | 7 | 8 |
| new utilities # | No | No | No | No | No | No |
| biological assays # | No | No | No | No | No | No |

SEQ ID Nos: 3-8 are immodulator core sequences derived from IGFBP1-6;
* U.S. Pat. Nos. 6,861,406/6,887,851/6,914,049/7,371,813/7, 611,893/7,618,816/7,662,624/8,536,135/10,369,191 and scientific references cited therein;
as demonstrated in the examples provided herein;

Whether immodulator peptides derived from IGFBPs other than IGFBP-3 exhibit similar or overlapping biological activities has not been previously disclosed. Mutations in the corresponding sequences of parent IGFBP1-6 molecules have implicated some of these core sequences in the actions of IGFBPs, including binding to importins and nuclear receptors, and extracellular matrix components such as glycosaminoglycans, transferrin receptor, and collagen. However, the sufficiency of immodulator peptide sequences for these functions remains unproven.

In the present invention, the range of usefulness of immodulator peptides has been surprisingly extended by covalent modification of the amino terminus of the peptide via chemical linkage to a small molecule. Such modifications to immodulator core sequences (covalent linkage to carboxylic acids other than proteinogenic amino acids or biotin) has not been previously disclosed. As set out in this invention, success in the creation of such novel conjugates by chemical methods is not straightforward to predict. Excluding proteinogenic amino acids or biotin, many small molecules of mass below one thousand daltons having a free carboxyl group in their chemical structure are too unstable to serve as adequate candidates for coupling under harsh conditions of peptide synthesis. Thus, success in the creation of this new class of chemically modified peptides under industrially useful manufacturing conditions is trial-based and not obvious. Novel compositions resulting from this class of chemical modifications to immodulator peptides, including peptides derived from an IGFBP-3-derived core sequence, are therefore new and non-obvious.

As disclosed in the present invention, new properties associated with metal binding are described. Although some metal binding properties of peptides containing SEQ ID NO: 5 had previously been demonstrated, this invention shows, for the first time, that peptide complexes to metals or metallocenes can be isolated in purified form. Moreover, the binding of metals has not previously been shown for modified peptides provided by the invention. Unexpectedly, immodulator peptide-metal complexes show novel and highly relevant biological activities both in vitro and in vivo. This invention also discloses binding of immodulator peptides to new metals. Furthermore, this invention discloses sequence modifications that substantially increase the affinity of immodulator peptides for binding metal.

This invention discloses new compositions and improved utilities of the immodulator peptide class: by chemical modification as set out in the paragraphs above, and by expanding the range of core sequences to include those derived from IGFBPs other than IGFBP-3 (SEQ ID NOs:3, 4, 6, 7, 8). Sequence extensions to immodulator core sequences disclosed in the invention confer new biological activities useful in treating human disease and in cosmetic applications (for example protein kinase-inhibiting peptide sequences described in U.S. Pat. Nos. 5,519,003/5,783,405/ 6,165,977/6,262,023/6,342,368/6,423,684/6,855,693/6,933, 275/7,393,835 and references cited therein).

Methods disclosed in this invention include the administration of pharmaceutical compositions containing immodulator peptides to a mammal showing temporary or long-term symptoms of immune system dysfunction or perturbation that may be linked to disease conditions, including but not limited to metabolic and cardiovascular diseases (especially those characterized by some underlying combination of insulin resistance, hyperglycemia, hypertension and hyperlipidemia); cancer progression and metastasis; acute kidney injury (AKI) in critical care settings, sepsis, systemic inflammatory conditions such as shock, post-operative oxidative stress such as after cardiopulmonary bypass or transplant, burns, blunt trauma, pancreatitis, rhabdomyolysis, xenobiotic stresses caused by cocaine, nicotine, alcohol, aminoglycoside antibiotics, cyclosporins, antiviral compounds or chemotherapeutic agents such as platinum compounds or doxorubicin; neuropathic pain and migraine; neurodegenerative diseases such as major depression, Parkinson's, Alzheimer's, Huntington's and ALS/Lou Gehrig's disease; immunosuppression phenomena; chronic obstructive pulmonary disease and other pulmonary diseases; pathological angiogenesis; impaired wound healing; ototoxicities; autoimmune conditions such as lupus erythematosus, arthritis, psoriasis, colitis, fibromyalgia, and multiple sclerosis; genetic diseases such as immune insufficiencies; cystinosis, Fanconi's and other conditions affecting mitochondrial respiration; other forms of mitochondrial dysfunction of bioenergetic failure; migraine; pulmonary diseases, especially chronic obstructive pulmonary disease, pulmonary arterial hypertension and asthma; ocular diseases such as cataracts and retinopathies, especially diabetic complications; and conditions caused by infectious agents, including chronic viral infections such as hepatitis, influenza and coronavirus.

In one aspect, the invention provides a modified peptide, 20-60 amino acids in length, comprising: (i) an insulin-like-growth-factor-binding-protein-derived immodulator core amino acid sequence comprising an amino acid sequence corresponding to SEQ ID NO:1 or SEQ ID NO:2; and (ii) a small molecule of molecular mass less than one thousand daltons linked covalently to the amino terminus of the amino acid sequence.

In some embodiments the small molecule is a carboxylic acid that is not an amino acid or biotin selected from the group consisting of: oleic acid, eicosapentanoic acid, lauric acid, decanoic acid, lignoceric acid, docosahexanoic acid, 2-hydroxy-2-decenoic acid, phenolic acids, anthraquinones, pentacyclic triterpenoids, retinoic acids, adapalene, bexarotene, rhein, proprionic acids, keto acids, cinnamic acids, aromatic carboxylic acids, indoleacetic acids, xanthenes, xanthones, fenofibric acid, valproic acid, 2-hexyl-4-pentynoic acid, 2,7-dichlorodihydro-fluorescein diacetate, indolyl-carboxylic acids, ibuprofen, artemisinic acid, metallocenes and bromopyruvic acid.

In some embodiments of the modified peptide the amino acid sequence of said immodulator core amino acid sequence consists of the amino acid sequence of any of SEQ ID NOs: 1-8. In some embodiments the modified peptide further includes an immodulator core sequence extended at its carboxyterminal end by amino acids ZV, where "Z" is any amino acid except L-cysteine or L-alanine. In other embodiments Z is D-alanine, glycine or any of the D- or L-isomers of serine, arginine, lysine, aspartic acid, glutamic acid, phenylalanine. In other embodiments the modified peptide further includes an amino acid sequence selected from the group consisting of: SEQ ID NOs: 10-22.

In some embodiments a modified peptide described herein is complexed with a metal selected from the group consisting of: ferrous iron, ferric iron, metallocenes such as ferrocene and derivatives thereof, zinc, copper, vanadium, ruthenium, cobalt, titanium, manganese, and calcium.

In some embodiments a modified peptide described herein is complexed with a glycosaminoglycan selected from the group consisting of: heparin, heparan sulfate, chondroitin sulfate, keratan sulfate, dermatan sulfate, and hyaluronate.

In a related aspect the invention provides a pharmaceutical composition that includes any modified peptide or modified peptide complex described herein, and a pharmaceutically acceptable excipient.

In yet another related aspect the invention provides a method for treating a subject suffering from immune dysfunction or perturbation, where the method includes administering to the subject (e.g., a human subject) a therapeutically effective dose of a modified peptide, a modified peptide complex, or a pharmaceutical composition as described herein. In a related aspect the invention provides the use of any modified peptide, modified peptide complex, or pharmaceutical composition described herein in the manufacture of a medicament for treatment of a subject suffering from immune dysfunction or perturbation. In some embodiments the immune dysfunction or perturbation to be treated includes one or more of abnormal catabolism, immunosuppression, oxidative stress, compromised organ function, compromised wound healing, hyperinflammation, infection, loss of glycemic control, accelerated neurodegeneration, or tumor growth and metastasis. In some embodiments the therapeutically effective dose of the modified peptide or modified peptide conjugate is from about 0.01 mg/kg/day to about 50 mg/kg/day.

In yet another related aspect the invention provides an in vitro method for measuring any modified peptide or modified peptide complex described herein, where the method includes determining the ability of the modified peptide or modified peptide complex to modulate Toll-like receptor (TLR) signaling, retinoic acid-inducible gene I (RIG-I) signaling, apoptosis, or collagen synthesis in cultured cells.

The compositions of the invention may be administered by means that include but are not limited to intravenous, oral, subcutaneous, intraarterial, intramuscular, intracardial, intraspinal, intrathoracic, intraperitoneal, intraventricular, sublingual, transdermal, and inhalation.

DETAILED DESCRIPTION

The terms "subject" and "individual", as used herein, refer to a vertebrate individual, including avian and mammalian individuals, and more particularly to sport animals (e.g., dogs, cats, and the like), agricultural animals (e.g., cows, horses, sheep, and the like), and primates (e.g., humans).

The term "treatment" is used herein as equivalent to the term "alleviating", which, as used herein, refers to an improvement, lessening, stabilization, or diminution of a symptom of a disease or immune perturbation. "Alleviating" also includes slowing or halting progression of a symptom.

As used herein, "co-administration", "in conjunction with", "concurrent", or "concurrently", as used interchangeably herein, refers to administration of one treatment modality in addition to another treatment modality. As such, "in conjunction with" refers to administration of one treatment modality before, during or after delivery of the other treatment modality to the subject.

Proteinogenic amino acids are amino acids that are incorporated biosynthetically into proteins during the process of translation by ribosomes inside a living cell. The proteinogenic amino acids are: alanine, cysteine, aspartic acid, glutamic acid, phenylalanine, glycine, histidine, isoleucine, lysine, leucine, methionine, asparagine, pyrrolysine, proline, glutamine, arginine, serine, threonine, selenocysteine, valine, tryptophan and tyrosine.

This invention claims a substantially purified 20-60 amino acid synthetic peptide comprising an insulin-like-growth-factor-binding-protein-derived immodulator core sequence. For the purposes of this invention, the "core sequence" comprised in the claimed immodulator peptides is either SEQ ID NO:1 or SEQ ID NO:2. This core sequence represents conserved residues derived from IGFBPs 1 through 6, and serves as the scaffold for immodulator peptides. In some embodiments, the above core sequence is C-terminally extended by the dipeptide ZV, where Z is any amino acid except cysteine. More preferably, Z is any amino acid except cysteine or L-alanine.

This invention provides a peptide having an amino terminus formed by covalent linkage to a carboxylic acid of molecular mass less than one thousand daltons, preferably less than five hundred daltons, wherein said carboxylic acid that is not an amino acid or biotin, and is selected from a group consisting of oleic acid, eicosapentanoic acid, lauric acid, decanoic acid, lignoceric acid, docosahexanoic acid, 2-hydroxy-2-decenoic acid, phenolic acids, anthraquinones, pentacyclic triterpenoids, retinoic acids, adapalene, bexarotene, rhein, proprionic acids, keto acids, cinnamic acids, aromatic carboxylic acids, indoleacetic acids, xanthenes, xanthones, fenofibric acid, valproic acid, 2-hexyl-4-pentynoic acid, 2,7-dichlorodihydro-fluorescein diacetate, indolyl-carboxylic acids, ibuprofen, artemisinic acid metallocenes such as ferrocene carboxylic acid and bromopyruvic acid.

The invention provides a modified immodulator peptide according to the above, wherein said immodulator core sequence is selected from a group consisting of SEQ ID NOs: 3-8. In some embodiments, said core sequence is C-terminally extended by the dipeptide ZV wherein Z is any amino acid except cysteine. Preferably Z is glycine, D-alanine, or any of the D- or L-isomers of serine, arginine, lysine, aspartic acid, glutamic acid or phenylalanine.

The invention further claims an immodulator peptide according to the descriptions above further comprising a sequence selected from a group consisting of sequence IDs 10-22.

In some embodiments, the invention provides a therapeutic immodulator peptide complexed with metal, wherein said metal is selected from a group consisting of ferrous iron, ferric iron, zinc, copper, vanadium, ruthenium, cobalt, titanium, manganese, and calcium, or metallocene compounds containing these metals. In other embodiments, the invention provides a therapeutic immodulator peptide complexed with a glycosaminoglycan selected from the group consisting of heparin, heparan sulfate, chondroitin sulfate, keratan sulfate, dermatan sulfate, and hyaluronate.

In another aspect, the invention provides a method for treating a mammal showing symptoms of immune dysfunction or perturbation comprising administering to said mammal via intramuscular, subcutaneous, parenteral, transdermal, intranasal, intravenous or intrathecal route of administration a pharmaceutical formulation comprising a therapeutically effective dose of an improved immodulator peptide according to the invention, and a pharmaceutically acceptable excipient, thereby alleviating said symptoms of dysfunction. In some embodiments, the immodulator peptide is administered in a therapeutically effective dose of peptide between about 0.01 mg/kg/day to about 50 mg/kg/day.

In another aspect, the invention provides for co-administration of a helper molecule that modulates the activity of cellular antiviral defenses. Preferably, said helper molecule is a modulator of the activity of cellular antiviral defenses, said helper selected from the group consisting of modulators of RIG-I, MDA5, MAVS, STING, IRF3, STAT1, STAT3, TBK1, PACT, LGP2, NFkappaB, DNA methylases such as 5-azacytidine or SAHA and toll-like receptors. Demethylation of DNA can derepress endogenous retroviral sequences which then, in turn, trigger cellular antiviral defense mechanisms. Preferably, the helper molecule is an agonist of RIG-I or MDA5 such as poly(I:C). Many agonists and enhancers of helper molecules are well-known in the art such as KIN-1400, a synthetic RIG-I agonist commercially available from Cayman Chemical (Ann Arbor, MI).

This invention envisages an in vitro assay method for measuring the biological potency of an immodulator peptide, said assay method selected from a group consisting of modulation of TLR signaling, RIG-I signaling, apoptosis or collagen synthesis in cultured cells. As will be understood by those of skill in the art, the mode of detection of a diagnostic signal will depend on the exact detection system utilized in the assay. For example, if a fluorescent detection reagent is utilized, the signal will be measured using a technology capable of quantitating the signal from the sample, such as by the use of a fluorometer. If a chemiluminescent detection system is used, then the signal will typically be detected using a luminometer. Methods for detecting signal from detection systems are well known in the art and need not be further described here.

Sequence "identity" and "homology", as referred to herein, can be determined using BLAST, particularly BLASTp as implemented by the National Center for Biotechnology Information (NCBI), using default parameters. It will be readily apparent to a practitioner skilled in the art that sequences claimed hereunder include all homologous and trivial variants of an immodulator peptide, such as by conservative substitution, extension and deletion in their amino acid sequences. Trivial substitution variants include swapping of an amino acid with another belonging to the same class, without such substitution resulting in any significant and measurable functional improvement. "Classes" of amino acids include positively charged amino acids (arginine, lysine, histidine), negatively charged amino acids (aspartic acid, glutamic acid), aromatic amino acids (tyrosine, phenylalanine, tryptophan), branched chain amino acids (valine, leucine isoleucine) and other natural groupings such as (serine, threonine) and (asparagine, glutamine).

For testing efficacy of pharmaceutical composition containing an immodulator peptide, an effective amount of therapeutic agent is administered to a subject having a disease. In some embodiments, the agent is administered at about 0.001 to about 40 milligrams per kilogram total body weight per day (mg/kg/day). In some embodiments the agent is administered at about 0.001 to about 40 mg/kg/day, e.g., 0.01, 0.015, 0.02, 0.05, 0.1, 0.2, 0.5, 0.7, 1, 2, 4, 5, 7, 9, 10, 15, 20, 25, 30, 35 or another dose from about 0.001 mg/kg/day to about 40 mg/kg/day.

Therapeutic agents are preferably administered via oral or parenteral administration, including but not limited to intravenous (IV), intra-arterial (IA), intraperitoneal (IP), intramuscular (IM), intracardial, subcutaneous (SC), intrathoracic, intraspinal, intradermal (ID), transdermal, oral, sublingual, inhaled, and intranasal routes. IV, IP, IM, and ID administration may be by bolus or infusion administration. For SC administration, administration may be by bolus, infusion, or by implantable device, such as an implantable minipump (e.g., osmotic or mechanical minipump) or slow release implant. The agent may also be delivered in a slow release formulation adapted for IV, IP, IM, ID or SC administration. Inhaled agent is preferably delivered in discrete doses (e.g., via a metered dose inhaler adapted for protein delivery). Administration of a molecule comprising an agent via the transdermal route may be continuous or pulsatile. Administration of agents may also occur orally. For parenteral administration, compositions comprising a therapeutic agent may be in dry powder, semi-solid or liquid formulations. For parenteral administration by routes other than inhalation, the composition comprising an agent is preferably administered in a liquid formulation. Compositions comprising an agent formulation may contain additional components such as salts, buffers, bulking agents, osmolytes, antioxidants, detergents, surfactants, and other pharmaceutical excipients as are known in the art.

As will be understood by those of skill in the art, the symptoms of disease alleviated by the instant methods, as well as the methods used to measure the symptom(s) will vary, depending on the particular disease and the individual patient. All references cited in this document, including patent applications and publications cited therein, are incorporated by reference in their entirety.

EXAMPLES

Example 1. N-Terminal Modification of Peptide with Carboxylic Acids of Molecular Mass Below 500 Daltons that are not Proteinogenic Amino Acids or Biotin

| Class | Compound | CAS No. | MW | Yld T4* | Yld IM3* |
|---|---|---|---|---|---|
| fatty acid | oleic acid | 112-80-1 | 282.5 | 44.21% | |
| fatty acid | eicosapentaenoic acid | 10417-94-4 | 302.5 | 66.79% | |
| fatty acid | lignoceric acid | 557-59-5 | 368.6 | 89.20% | |
| fatty acid | decanoic acid | 1002-62-6 | 172.2 | 88.67% | 98.0% |
| fatty acid | docosahexanoic acid | 6217-54-5 | 368.6 | 57.77% | |
| fatty acid | lauric acid | 143-07-7 | 200.3 | 85.14% | 96.7% |
| fatty acid | 10-hydroxy-2-decenoic acid | 14113-05-4 | 186.3 | 44.38% | |
| phenolic acid | ferulic acid | 1135-24-6 | 194.2 | 26.58% | |
| phenolic acid | isoferulic acid | 537-73-5 | 194.2 | 55.80% | 70.2% |
| phenolic acid | Aspirin | 50-78-2 | 180.2 | 56.5% | |
| phenolic acid | valeroyl salicylate | 64206-54-8 | 222.2 | 11.76% | |

-continued

| Class | Compound | CAS No. | MW | Yld T4* | Yld IM3* |
|---|---|---|---|---|---|
| pentacyclic triterpenoid | betulinic acid | 472-15-1 | 456.7 | <1% | |
| anthraquinone | Rhein | 478-43-3 | 284.2 | 50.95% | |
| anthraquinone | Diacerein | 13939-02-1 | 368.3 | 43.2% | |
| Xanthone | 2,7-dichlorodihydro-fluorescein diacetate | 4091-99-0 | 487.3 | 91.2% | |
| proprionic acid | (s)-ketoprofen | 22161-81-5 | 254.3 | 77.86% | |
| proprionic acid | Ibuprofen | 15687-27-1 | 206.3 | 93.42% | 98.0% |
| carboxylic acid | trans-cinnamic acid | 140-10-3 | 148.2 | 93.12% | 81.5% |
| carboxylic acid | (s)-(−)-perillic acid | 23635-14-5 | 166.2 | 27.96% | |
| carboxylic acid | fenofibric acid | 42017-89-0 | 318.8 | 85.67% | 99.9% |
| indoleacetic acid | Indomethacin | 53-86-1 | 357.8 | 87.5% | 85.2%# |
| pentanoic acid | valproic acid | 1069-66-5 | 144.2 | 91.43% | 84.9% |
| alkynoic acid | 2-hexyl-pentynoic acid | 96017-59-3 | 182.3 | | 85.1% |
| indolylcarboxylic | RG-108 | 48208-26-0 | 334.3 | | 74.3%@ |
| Retinoid | all-trans retinoic acid | 302-79-4 | 300.4 | 13.1% | |
| Rexinoid | Bexarotene | 153559-49-0 | 348.5 | 97.09% | 94.4% |

Covalent terminal conjugation of carboxylic acids to peptides.
*Percent yield of correct species by MS for T4 (tetrapeptide) and IM3 immodulator peptide (industrially desirable >80% shown in bold type);
lost p-chlorophenone group (incorrect product);
@indole core oxidized by Arg protecting groups (incorrect product);

N-terminal modification of peptides with biotin, or fatty acids such as myristic and palmitic acids, has been commonly disclosed in the literature. Other types of carboxylic acids have rarely, if ever, been used in this way. This example shows the difficulty in predicting success for this type of modification for a previously untried carboxylic acid without doing the actual experiment. The data in this example disclose, amongst other facts: (i) coupling to carboxylic acids (that are not proteinogenic amino acids or biotin) using normal peptide synthesis conditions; (ii) surprising results showing that yields of correctly coupled product (as ascertained by mass spectroscopy analysis) varied greatly, even within the same class of compound; and (iii) consistent results for small molecules attached by this method to immodulator peptide IM3 (SEQ ID NO:17) or a generic D-tetrapeptide KDKP with similar efficiencies of coupling to either peptide, thereby demonstrating the generality of the method. Peptides were synthesized according to a common Fmoc/tBu solid phase synthesis strategy well-known in the art. Synthesis may be manual of automated. After the peptide synthesis the resin was divided into batches of 20 umol. Each batch was treated with one of the organic compounds specified in Table x1B below. The coupling was carried out using 2 equivalents of the compound, 2.4 equivalents of activator HATU or HCTU, and 4 equivalents of NMM base. The reaction mixture was renewed after 2 hrs reaction time and allowed to react another 4 hrs or overnight. After washing the resin several times with DMF, and subsequently with DCM, the batches were dried. For the cleavage of the peptides from the resin the resins were treated with 1% DTT, 2% water and 3% TIPS in TFA for 3.5 hrs. The cleavage solution was separated from the resin and treated with diethylether/n-pentane (1:1). The resulting precipitate was centrifuged and the pellet washed three times in the same DEE/pentane mixture. The recovered peptide was air dried and stored at −20 degrees C. or further purified by HPLC using a 0-50% acetonitrile gradient, 0.1% trifluoroacetic acid (20 min). The results of the above conjugation experiments show that, both inter-class and intra-class, there is wide variation in conjugation efficiency from compound to compound. As the practicality and cost of synthesis can be dramatically affected when product yield is low, it is therefore not obvious that any untested carboxylic acid should be assumed to be a good candidate for this type of peptide modification. The use of most of the compounds tested here has never been reported for this kind of peptide modification. It appears that that chance of practical success (>80% correct yield, for instance) for each instantiation of this technology is less than 50% until tested.

Example 2. Metal Binding

The following peptides were used in experiments involving streptavidin-coated plates or Alexa488-labeled streptavidin reagent (N-terminally biotinylated versions in some instances). The sequences of these peptides, shown in parentheses) comprise the SEQ ID NOs shown after each sequence:

```
IM1
                                             SEQ ID NO: 15
(KNGFYHSRQCETSMDGEAGLCW)

IM2
                                             SEQ ID NO: 16
(KHGLYNLKQCKMSLNGQRGECW)

IM3
                                             SEQ ID NO: 17
(KKGFYKKKQCRPSKGRKRGFCW)

IM4
                                             SEQ ID NO: 18
(RNGNFHPKQCHPALDGQRGKCW)

IM5
                                             SEQ ID NO: 19
(RKGFYKRKQCKPSRGRKRGICW)

IM6
                                             SEQ ID NO: 20
(HRGFYRKRQCRSSQGQRRGPCW)

IM3N1
                                             SEQ ID NO: 21
(RGVTEDYLRLETLVQKVVSKGFYKKKQCRPSKGRKRGFCW)

IM3N2
                                             SEQ ID NO: 22
(TGPSESYLQLEELVKQVVSKGFYKKKQCRPSKGRKRGFCW)
```

```
IM3AVD:
                                           SEQ ID NO: 23
KKGFYKKKQCRPSKGRKRGFCWAVD

IM3dAVD:
KKGFYKKKQCRPSKGRKRGFCW(dA)VD

IM3FVS:
                                           SEQ ID NO: 25
KKGFYKKKQCRPSKGRKRGFCWFVS
```

Experiment x2A. Metal-Immodulator Peptide IM3N1 Binding (Detection by ELISA)

The NTA-metal-affinity ELISA assay was performed using 96-well NTA-metal-coated plates readily available from commercial sources such as Qiagen (Germantown, MD). The NTA was charged with ferrous or ferric iron, zinc, copper, calcium, vanadium, ruthenium, cobalt, titanium, manganese or other metals. 400 ng of immodulator peptide IM3N1 in PBS buffer was added per plate. After incubation at room temperature for 60 minutes, excess peptide was washed off and peptide was detected by ELISA using an anti-immodulator rabbit primary antibody (A2501) and horseradish peroxidase conjugated to a secondary anti-rabbit antibody (arbitrary units)*vs EDTA control:

EDTA (no metal): 0.047±0.001
Fe2+ (Ferrous): 0.844±0.026 (p<0.001*)
Fe3+ (Ferric): 0.848±0.011 (p<0.001*)
Zn2+ (Zinc): 0.194±0.089 (p<0.05*)
Cu2+ (Copper): 0.229±0.086 (p<0.05*)

Experiment x2B. Metal-Immodulator Peptide Binding (Detection by Fluorescence)

NTA-metal-affinity fluorescence assay was performed using 96-well NTA-metal-coated plates readily available from commercial sources such as Qiagen (Germantown, MD). NTA was charged with ferrous or ferric iron, zinc, copper, calcium, vanadium, ruthenium, cobalt, titanium, manganese or other metals. 400 ng of FITC-labeled immodulator peptide (or biotinylated immodulator peptide complexed to Alexa-488-labeled streptavidin) in PBS buffer was added per plate. After incubation at room temperature for 60 minutes, excess peptide was washed off and peptide was detected by measuring fluorescence (excitation 490 nm, emmission 525 nm) in a fluorometer.

(a) Using FITC-labeled IM3 peptide (1 ug/well) in the fluorescent binding assay:

EDTA-treated control: 2,251±1,186
Ferrous iron: 170,441±11,264 (p<0.001)*
Copper: 13,644±5566 (p<0.05)*
Calcium: 48,822±11,990 (p<0.01)*
*p values are relative to EDTA-treated control (b) Competition binding assay to ferrous iron, calcium, copper and zinc-charged NTA-coated plates using FITC-labeled IM3 peptide (0.5 uM) and 8× (4 uM) unlabelled competitor peptides IM3N1, IM3N2 (*all comparisons to PBS control are p<0.01); # fluorescent value of binding to calcium was set at 100.

| Metal | Compet: PBS | Compet: IM3N1 | Compet: IM3N2 |
|---|---|---|---|
| Calcium # | 100.0 ± 1.9 | 14.6 ± 1.4* | 12.9 ± 1.2* |
| Ferrous iron | 85.6 ± 5.8 | 20.4 ± 1.0* | 25.2 ± 9.5* |
| Copper | 53.0 ± 0.6 | 9.2 ± 1.5* | 5.1 ± 1.0* |
| Zinc | 85.9 ± 5.5 | 15.7 ± 1.3* | 13.4 ± 1.6* |

(c) Alexa488-SA-labelled immodulator peptide IM3 (400 ng/well) bound to NTA-coated plate charged with the indicated metals: # fluorescent value of binding to ferrous iron was set at 100. *p<0.01 relative to control.

Ferrous iron # (100±2.6*); Control (no metal): 6.4±3.1; Ferric iron: 94.1±6.6*; Calcium: 47.6±3.7*; Vanadium: 53.9±5.5*; Manganese: 54.4±11.2*; Cobalt: 25.4±2.3*; Copper: 58.4±6.4*; Zinc: 71.4±8.3*; Ruthenium: 67.8±8.3*; (d) Alexa488-SA-labelled immodulator peptide IM1, IM2, IM3, IM4, IM5, IM6 (400 ng/well) were bound to NTA-coated plate charged with the indicated metals: # background (no peptide) control set to 1.0;*p<0.05, **p<0.01 vs "no peptide"

| Peptide | Ferrous iron | Calcium | Copper | Zinc |
|---|---|---|---|---|
| IM1 | 1.2 ± 0.3 | 1.1 ± 0.1 | 3.0 ± 0.1** | 1.1 ± 0.2 |
| IM2 | 1.4 ± 0.3 | 1.7 ± 0.2* | 3.6 ± 0.1** | 1.1 ± 0.1 |
| IM3 | 24.7 ± 1.6** | 28.7 ± 0.7** | 6.2 ± 0.2** | 32.0 ± 0.7** |
| IM4 | 2.8 ± 1.4 | 1.0 ± 0.1 | 5.7 ± 0.1** | 1.2 ± 0.2 |
| IM5 | 20.5 ± 1.5** | 23.4 ± 0.8** | 5.6 ± 0.1** | 23.6 ± 0.1** |
| IM6 | 20.6 ± 0.8** | 15.1 ± 1.9** | 2.4 ± 2.4** | 8.4 ± 0.4** |
| No peptide # | 1.0 ± 0.1 | 1.0 ± 0.0 | 1.0 ± 0.2 | 1.0 ± 0.1 |

Experiment x2C. Binary Peptide-Metal Complexes

Preparation of binary peptide-metal complexes in PBS buffer was performed by incubating 4 mg of IM3N1 peptide in 5 mM metal solution at room temperature for 60 min. The mixture was desalted using a GT-100 SpinOUT column (G-Biosciences Inc, St. Louis, MO) equilibrated in PBS buffer. Recovery of peptide was 30-35% for zinc and iron complexes. In the case of iron, confirmation of metal within the complex per mg peptide was made using a commercial kit for iron assay. Additionally, peptide-metallocene complex were prepared using IM3 peptide and a ferrocene derivative, ferroquine (purchased from Sigma-Aldrich, St. Louis, MO).

Experiment x2E. Immodulator Peptide Variants Showing Enhanced Metal Binding

Immodulator peptides were extended C-terminally by three amino acids, to include a valine residue that is highly conserved in the "thyroglobulin type 1 motif". The reasoning behind this attempt is that a longer conserved sequence might lead to a tighter fold overall, which might in turn result in increased metal-binding avidity.

(b) Strength of binding to iron was evaluated by plate assay.

Experiments were conducted by the procedure described above. Ferric iron-charged NTA-coated 96-well plates were used as described. 1 ug/well immodulator peptide complexed to Alexa-488-labeled streptavidin in PBS buffer was added (60 min at room temperature). The plate was washed and counted in a standard fluorometer (excitation/emission: 485/525 nm). The results (fluorescence) show improved iron-binding by the three peptides extended C-terminally by the AVD, (dA)VD, and FVS tripeptides. **p<0.01 vs IM3 control IM3: 200±29; IM4: 45±37; IM5: 130±77; IM3AVD: 434±29; IM3dAVD: 418±28; IM3FVS: 371±33

(c) Competition assay. The same procedure was used as the preceding experiment, except that 375 ng/well labeled IM3 peptide was used, plus 10× of the indicated unlabeled peptide. 'No competing peptide' control value was set to 100. *p<0.05 vs "no peptide" control
Competing Peptide/Fluorescence
None: 100±38; IM4: 125±26; IM3: 63±27*; IM5: 40±14*; IM3AVD: 10±28*

(d) Competition assay. The same procedure was used as the preceding experiment, except that labeled IM3AVD peptide was used. **p<0.01 vs "no competing peptide" control
None: 100±9; IM4: 144±44; IM3: 35±16; IM5: 30±19; IM3AVD: 9±19**

(e) The same procedure was used as the preceding experiment, except that each peptide was labeled with Alexa-488-labeled streptavidin in PBS buffer and used separately. Binding to IM3 was set to =100. *p<0.05, p<0.01 vs IM3 control. (Labeled Peptide/Fluorescence) IM1: 1.8±0.4; IM2: 3.0±1.8**; IM3: 100.0±16.8; IM4: 7.2±1.7*; IM5: 86.7±6.4; IM6: 85.9±14.9; IM3AVD:137.7±11.8*; IM3dAVD: 147.4±22.9*; IM3FVS: 101.5±10.5. The results of the above experiments show that when the IM3 sequence is extended C-terminally by the AVD tripeptide, iron is bound more tightly.

Example 3. Additional Novel Properties of Immodulator Peptides

Experiment x3A

Binding of immodulator peptides to AA111-228 DNA-binding domain of RXR-alpha (RXRa-DBD). 1 ug/well recombinant RXRa-DBD (Abcam, Cambridge, MA) was adsorbed to wells of a 96-well plate for 60 minutes at RT, then blocked with 200 uL 1% BSA in PBS buffer overnight. Plate was washed and 800 ng/well Streptavidin-Alexa 488 conjugate (SA488)-labelled IM peptide was added. The plate was incubated for 60 min at room temperature, washed and counted in a standard fluorometer (excitation/emission 485/525 nm). Background (buffer alone) was subtracted. The results are shown in Table x3A. They show that IM3, IM5 and IM6 bind RXRa-DBD. *p<0.05, **p<0.01 vs no peptide; (Peptide/Fluorescence) IM1: 670±85*; IM2: 2±38; IM3: 6,572±129; IM4: 27±31; IM5: 6,802±336; IM6: 587±192*; No peptide: 8±232.

Experiment x3B. Binding of immodulator peptides to DNA-binding domain (DBD) of RXR-alpha, with or without ferric iron. 100 ng/well recombinant RXRa-DBD (Abcam, Cambridge, MA) was adsorbed to wells of a 96-well plate for 60 minutes at RT, then blocked with 200 uL 1% BSA in PBS buffer overnight. Plate was washed and 800 ng/well Streptavidin-Alexa 488 conjugate (SA488)-labelled IM peptide was added, with or without ferric chloride (5 uM) or 5-fold excess RXRa-DBD. The plate was incubated for 2 hours at room temperature, washed and counted in a standard fluorometer (excitation/emission 485/525 nm). The results are shown in Table x3B. They show that IM3 and IM5 bind RXRa-DRD iron stimulates this binding and cold RXRa-DRD combates against it

| Peptide | FeCl3 | excess RXRa-DBD | Fluorescence |
|---|---|---|---|
| None | None | None | 88.0 ± 9.8 |
| IM3 | None | None | 687.3 ± 55.4**## |
| IM3 | 5 uM | None | 1161.3 ± 78.5 |
| IM3 | 5 uM | 5X | 837.0 ± 30.5 # |
| IM5 | None | None | 228.0 ± 44.9* |
| IM5 | 5 uM | None | 552.7 ± 86.8 |
| IM5 | 5 uM | 5X | 303.0 ± 68.3 # |

*p < 0.05,
**p < 0.01 vs no peptide;
# p < 0.05,
p < 0.01 vs binding with iron

Experiment x3C. Binding of Immodulator Peptides to Full-Length huNur77

400 ng/well recombinant Nur77 (Abcam, Cambridge, MA) was adsorbed to wells of a 96-well plate for 90 minutes at RT, then blocked with 200 uL 1% BSA in PBS buffer overnight. Plate was washed and 333 ng/well Streptavidin-Alexa 488 conjugate (SA488)-labelled IM3, IM4 or no peptide was added. The plate was incubated for 60 min at room temperature, washed and counted in a standard fluorometer (excitation/emission 485/525 nm). Background (buffer alone) was subtracted. The results are shown in Table x3C. They show that IM3 but not IM4 binds Nur77. **p<0.01 vs IM3+Nur77; #p<0.01 vs no peptide+no Nur77 control;

| Peptide | Nur77 | Fluorescence |
|---|---|---|
| None | None | 63 ± 34 |
| None | 400 ng | 98 ± 59** |
| IM3 | None | 59 ± 17 |
| IM3 | 400 ng | 488 ± 38 # |
| IM4 | None | 112 ± 24 |
| IM4 | 400 ng | 70 ± 48** |

Experiment x3D. Binding of Immodulator Peptides to Glycosaminoglycan, Heparin 1 ug Streptavidin-Alexa 488 conjugate (SA488)-labelled IM peptide in PBS buffer was loaded on a spin column packed with 0.2 ml bed volume heparin-agarose (G-Biosciences, St. Louis, MO). The column was centrifuged for 2 min at 2,000 G and the flow-through was collected. The column was then washed with 0.3 ml 1% BSA in PBS buffer and the column spin repeated. Flowthrough and wash were pooled and duplicate 20 uL aliquots counted in a standard fluorometer (excitation/emission 485/525 nm). Results are expressed as percentage of input counts that bound the heparin-agarose column, versus flowthrough. Percent counts bound to heparin-agarose resin are shown below. IM3, IM5 and IM6 peptides bind heparin-agarose in this assay. The other 3 peptides do not.

| Peptide | Percent retained | Percent Flowthrough |
|---|---|---|
| None | 0 | 100.0 |
| IM1 | 0 | 100.0 |
| IM2 | 0 | 100.0 |
| IM3 | 97.7 | 2.3 |
| IM4 | 0 | 100.0 |
| IM5 | 96.4 | 3.6 |
| IM6 | 98.0 | 2.0 |

Example 4. Modulation of Key Immunological Pathways Using Immodulator Peptides Immune modulation functions of immodulator peptides were measured using the monocyte reporter cell line THP1-Dual (Invivogen, San Diego, CA), which provides convenient readouts for STING and NF-kappa-B pathways. Optionally, succinic acid, cytokine and chemokine production were also measured. THP1-Dual cell line was obtained from Invivogen. Cells were grown in a T-75 flask in RPMI Medium containing 20% fetal bovine serum, blasticidin (10 mg/mL), zeocin (100 mg/mL) and penicillin-streptomycin at 37° C. in a humidified, 5% CO2 incubator. Cells (100 ml, 8,000 cells/well) were plated in a 96-well plate and incubated overnight at 37ºC in a humidified, 5% CO2 incubator. Next day, 10 ml/well of compounds were added (quadruplicate wells). After 24 hour incubation with the compound, supernatants were harvested and stored at 4° C. prior to assay.

Experiment x4A. TLR- and RIG-I-Stimulating Activity of Immodulator Peptides in THP1-Dual Monocytes Each cell supernatant was assayed in quadruplicate. 20 uL of supernatant was used to measure NF-kappa-B (NFkB) and
STING activity using reagents QuantiBlu and QuantiLuc respectively, according to the manufacturer's recommendations (Invivogen, San Diego, CA). Succinic acid was measured by using a kit from Megazyme Inc (Cambridge, MA). The results of this experiment are shown in Tables x4A-D below. Control value of activity was set to 100 in each assay. The data show that the stimulating activity of various immodulator peptides is influenced by specific extension sequences and by the kind of N-terminally conjugated carboxylic acid. PAM3C=25 ng/ml PAM3CSK4 (TLR1/2 inducer); Poly(I:C)=10 ug/ml (TLR3 inducer); PAM2C=25 ng/ml PAM2CSK4 (TLR2/6 inducer); KIN14=4 uM KIN-1400 (RIG-I inducer); cytB=1 uM cytosporone B (Nur77 inducer); C-178=1 uM STING inhibitor; NFkBi=50 ug/ml NFkB inhibitor peptide; SB2021=10 uM p38MAPK inhibitor; *p<0.05, **p<0.01 vs IM3 control; #p<0.01 vs "no inducer" control; SUCC=succinic acid; nd=not done; Peptide was added to cells at 400 nM.

| Peptide | Inducer | Modulator | NFkB | STING | SUCC |
|---|---|---|---|---|---|
| | None | | 100 | 100 | Nd |
| IM3 | None | | 94** | 91** | nd |
| | PAM3C | | 326 # | 342 # | |
| IM3 | PAM3C | | 575 | 1474 | 100 |
| IM3 | PAM3C | cytB | 576 | 1318** | 95.4 |
| IM3 | PAM3C | C-178 | 561 | 566** | 95.3 |
| IM3 | PAM3C | NFkBi | 458** | 1294** | 101.5 |
| IM3 | PAM3C | SB2021 | 296** | 274** | 95.8 |

| Peptide | | Reagent | NFkB | STING | SUCC |
|---|---|---|---|---|---|
| | PAM2C | | 118.7** | 144.5** | 121.5* |
| IM3 | PAM2C | | 100 | 100 | 100 |
| IM3 | PAM2C | cytB | 99.8 | 96.5 | 85.1* |
| IM3 | PAM2C | C-178 | 108.0** | 62.0** | 96.1 |
| IM3 | PAM2C | NFkBi | 118.7* | 119.1* | 100.1 |
| IM3 | PAM2C | SB2021 | 65.4** | 18.9** | 93.4 |

Peptides were added to cells at 400 nM. Inducer was KIN1400 (RIG-I agonist).

| Peptide | Reagent | NFkB | STING | SUCC |
|---|---|---|---|---|
| | | 90.1 | 84.3** | 100.1 |
| IM3 | | 100 | 100 | 100 |
| IM3 | cytB | 103.5 | 87.5* | 96.1 |
| IM3 | C-178 | 98.1 | 81.1** | 103.2 |
| IM3 | NFkBi | 104.4 | 105.0 | 99.2 |
| IM3 | SB2021 | 131.3** | 75.6** | 131.6* |

Example 5. Positive Effects of Ferric Iron and Covalent Modification of Peptide on the Systemic Efficacy of Nephrilin IM3N1 Peptide in Burn Trauma Experiment x5A. Nephrilin peptide (IM3N1) is a designed inhibitor of Rictor complex (also known as mTORC2), an evolutionarily conserved assembly believed to modulate responses to cellular stress. We previously demonstrated the ability of nephrilin peptide to suppress neuroinflammation, loss of body mass, glycemic control and kidney function in a rat scald model, as well as sepsis mortality in a mouse model. This study explores the effect of nephrilin plus iron formulations on clinically relevant outcomes in the rat scald model. Animals were treated with nephrilin by subcutaneous bolus injection on days 1-7 post-burn. Equimolar ferric iron in the formulation improved the positive systemic effects of nephrilin on kidney function, glycemic control, oxidative stress, early hyperinflammation, late inflammasome activation, hyperangiogenesis and body mass, all variables previously shown to bear upon clinically relevant burn injury outcomes. The rat scald model and measurement of clinically relevant variables are disclosed in U.S. Pat. No. 10,369,191. Adult Sprague Dawley rats of both sexes (250-300 gm, Charles River Laboratories, Wilmington, MA, USA) were injected with nephrilin peptide plus or minus equimolar metal (zinc, ferrous iron or ferric iron) once daily by subcutaneous bolus injection, days 1-7; Treatment group sizes were (n=8) for each sex unless otherwise indicated: group S=sham-treated; group B=burn+vehicle; group N1=burn+4 mg/kg nephrilin; group N1/Zn2=burn+4 mg/kg nephrilin/zinc chloride; group N1/Fe2=burn+4 mg/kg nephrilin/ferrous sulphate; groups N1/Fe3 (2, 4 or 8)=burn+2, 4, or 8 mg/kg nephrilin/equimolar ferric chloride. The first dose was administered after completion of the scald procedure. Injection volume was 400 uL. Control animals received the same volume of vehicle.

Male Rats: Ferric Iron Improves Efficacy of Nephrilin Peptide

Table x5A1 shows the results obtained when male rats in the scald model were exposed to vehicle, 4 mg/kg nephrilin and 4 mg/kg nephrilin complexed with either ferric iron, ferrous iron or zinc. To make global comparisons of treatment efficacy, we converted values to z-scores. All scores within an efficacy class were averaged, allowing allocation of equal weight to efficacy classes. A composite z-score (average z score across all 7 effect classes) is shown in the last row of the table. This allows direct comparison of efficacy across treatment groups. The sham treatment involves manipulating the animals exactly as in the burn group, but without the burn treatment. The efficacy value for the sham (0.82) is thus the positive control. The negative control is the Burn+vehicle group (−0.61). The results show that ferric iron supplementation is superior to the other metals (efficacy of 0.27 vs 0.01 and −0.19 for zinc and ferrous iron, respectively) in improving the efficacy of nephrilin. Compared to vehicle or nephrilin treatment alone (−0.31), nephrilin with ferric iron (0.27) is at least twice as efficacious overall. Male rats in the scald model were exposed to vehicle, 2, 4 and 8 mg/kg nephrilin complexed with ferric iron. The results show that 2 mg/kg (0.17) and 4 mg/kg (0.27) dose levels were superior to 8 mg/kg (−0.37).

Control animals received the same volume of vehicle. Rat scald model was performed and measurements taken as described in Experiment x5A. The Table x5B (above) shows the results obtained when male rats in the scald model were exposed to vehicle, or 2 mg/kg peptide complexed with ferric iron: (V) valproic acid; (D) decanoic acid; (F) fenofibric acid; (I) ibuprofen; for left column, see legend to Table x5A; * $p<0.05$ vs burn+vehicle; #$p<0.05$ vs burn+IM3N1

TABLE x5A1

Efficacy in male rats. Treatment groups (n = 8) are described in Methods. Effect classes - 1: early inflammation (24-hr plasma IL-6 pg/ml); 2: 14-day plasma inflammasome markers (2a = IL18 pg/ml; 2b = IL1b pg/ml); 3: 14-day plasma hyperangiogenesis markers (3a = VEGF-A pg/ml; 3b = CCL5 pg/ml; 3c = CXCL5 pg/ml; 3d = PctRedPix); 4: glycemic control, 14-day GTT (AUC mg · dL · hr); 5: kidney function, 14-day plasma (creatinine mg/dL); 6: systemic oxidative stress, 14-day plasma (OHDG pg/ml); 7: weight loss (slope).

| x5A | S (Sham) | B (vehicle) | N1 4 mg/kg | N1/Zn2 4 mg/kg | N1/Fe2 4 mg/kg | N1/Fe3 2 mg/kg | N1/Fe3 4 mg/kg | N1/Fe3 8 mg/kg |
|---|---|---|---|---|---|---|---|---|
| 1 | 31.4 ± 12.0* | 62.3 ± 16.9 | 50.6 ± 6.1 | 43.4 ± 13.6* | 49.1 ± 13.1 | 38.5 ± 27.8 | 41.4 ± 11.2* | 48.5 ± 18.5 |
| 2a | 125.2 ± 45.5* | 203.8 ± 61.8 | 178.1 ± 19.3 | 133.3 ± 25.1 | 157.7 ± 70.7 | 220.4 ± 32.1 | 119.1 ± 15.4* | 148.2 ± 61.7 |
| 2b | 41.9 ± 12.3* | 266.8 ± 185.2 | 124.3 ± 132 | 36.7 ± 9.5* | 97.4 ± 86.6 | 52.9 ± 7.8* | 36.6 ± 7.8* | 254.5 ± 291.9 |
| 3a | 50.4 ± 10.2* | 67.4 ± 17.4 | 56.1 ± 11.7 | 38.3 ± 8.8* | 41.2 ± 6.8* | 37.8 ± 15.3* | 48.1 ± 10.9* | 43.3 ± 8.1* |
| 3b | 218.1 ± 41.8* | 664.8 ± 42.8 | 609.7 ± 283 | 321.1 ± 96 | 249.8 ± 73* | 248.3 ± 29.7* | 192.1 ± 26.3*#& | 301.2 ± 74.9 |
| 3c | 763 ± 229* | 2009 ± 745 | 1910 ± 380 | 1154 ± 224* | 939 ± 300*# | 855 ± 233*#& | 1038 ± 495* | 1435 ± 445 |
| 3d | n/a | 20.01 ± 1.37 | 16.51 ± 3.02 | 9.74 ± 5.79* | 11.79 ± 5.6* | 6.53 ± 3.16* | 8.65 ± 3.35*#& | 18.3 ± 11.83 |
| 4 | 78.4 ± 43.4* | 157.3 ± 69.8 | 139.3 ± 48.6 | 215.6 ± 124 | 120.6 ± 65.4 | 136.4 ± 69.2 | 94.3 ± 25.4* | 93.8 ± 37.2* |
| 5 | 0.23 ± 0.03* | 0.38 ± 0.18 | 0.34 ± 0.13 | 0.26 ± 0.12 | 0.38 ± 0.16 | 0.31 ± 0.09 | 0.18 ± 0.11*#& | 0.38 ± 0.12 |
| 6 | 479 ± 116* | 665 ± 78 | 585 ± 137 | 454 ± 76*# | 455 ± 71*# | 374 ± 187*#& | 423 ± 79*#& | 761 ± 89 |
| 7 | 5.58 ± 1.00* | 2.34 ± 1.03 | 2.32 ± 1.01 | 1.66 ± 1.08 | 2.65 ± 0.56 | 2.99 ± 0.53 | 2.71 ± 1.62 | 2.50 ± 0.55 |
| Avg | 0.82 ± 0.58* | −0.61 ± 0.47 | −0.31 ± 0.35 | 0.01 ± 0.62* | −0.19 ± 0.52* | 0.17 ± 0.40* | 0.27 ± 0.60*#& | −0.37 ± 0.45 |

*$p < 0.05$ vs B group;
$p < 0.05$ vs N1 group;
&$p < 0.05$ vs 8 mg/kg group.

Experiment x5B

Effect of N-terminal modifications on the efficacy of nephrilin IM3N1 peptide in the rat scald model. In this study, five nephrilin-iron binary complexes were compared: IM3N1 (unmodified) and the following: IM3N1vlp (valproic acid), IM3N1dec (decanoic acid), IM3N1fen (fenofibric acid), and IM3N1ibu (ibuprofen). Adult male Sprague Dawley rats (300 gm, Charles River Laboratories, Wilmington, MA, USA) were injected with peptides formulated with equimolar metal ferric iron once daily by subcutaneous bolus injection, days 1-7.

group. The results show that 2 mg/kg IM3N1vlp dose levels were superior to 2 mg/kg unmodified IM3N1 peptide.

Example 7. Transcriptional Re-Programming in Rat CNS Two Weeks after Burn Trauma: The Impact of Nephrilin IM3N1 Peptide Treatment on the Expression of Key Genes Associated with Oxidative Stress Survivors of severe burns suffer lifetime neuroinflammatory consequences manifested by higher incidence of major depression and neurodegenerative disease. In a scald model,

| x5B | Sham | Burn + Vehicle | Burn + IM3N1 | Burn + IM3N1vlp | Burn + IM3N1dec | Burn + IM3N1fen | Burn + IM3N1ibu |
|---|---|---|---|---|---|---|---|
| 1 | 31.4 ± 12.0* | 62.3 ± 16.9 | 38.5 ± 27.8 | 24.4 ± 19.2* | 35.4 ± 22.9 | 54.8 ± 29.6 | 68.9 ± 20.4 |
| 2a | 125.2 ± 45.5* | 203.8 ± 61.8 | 220.4 ± 32.1 | 142.4 ± 53.2 | 170.9 ± 25.2 | 183.7 ± 46.5 | 119.7 ± 50.6* |
| 2b | 41.9 ± 12.3* | 266.8 ± 185.2 | 52.9 ± 7.8* | 62.8 ± 17.2* | 53.2 ± 11.6* | 63.2 ± 14.9* | 43.2 ± 4.4* |
| 3a | 50.4 ± 10.2* | 67.4 ± 17.4 | 37.8 ± 15.3* | 44.3 ± 11.5* | 29.9 ± 8.7* | 38.3 ± 11.5* | 32.7 ± 15.3* |
| 3b | 218.1 ± 41.8* | 664.8 ± 42.8 | 248.3 ± 29.7* | 220.2 ± 43.4* | 243.1 ± 52.2* | 285.2 ± 104.3* | 202.1 ± 88.2* |
| 3c | 763 ± 229* | 2009 ± 745 | 855 ± 233* | 717 ± 324* | 717 ± 285* | 774 ± 232* | 589 ± 377* |
| 3d | n/a | 20.01 ± 1.37 | 6.53 ± 3.16* | 1.46 ± 0.87*# | 4.83 ± 3.17* | 5.30 ± 2.68* | 3.17 ± 1.5* |
| 4 | 78.4 ± 43.4* | 157.3 ± 69.8 | 136.4 ± 69.2 | 57.5 ± 40*# | 112.0 ± 55.9 | 114.9 ± 59.7 | 89.8 ± 71.6 |
| 5 | 0.23 ± 0.03* | 0.38 ± 0.18 | 0.31 ± 0.09 | 0.17 ± 0.03*# | 0.33 ± 0.11 | 0.29 ± 0.09 | 0.24 ± 0.07* |
| 6 | 479 ± 116* | 665 ± 78 | 374 ± 187* | 360 ± 121* | 597 ± 115 | 870 ± 265 | 712 ± 164 |
| 7 | 5.58 ± 1.00* | 2.23 ± 1.08 | 2.99 ± 0.53 | 3.74 ± 0.31*# | 3.40 ± 0.75 | 3.32 ± 0.76 | 3.55 ± 1.43 |

Treatment group sizes were (n=6) for each group: group S=sham-treated; group B=burn+vehicle; group N1=burn+2 mg/kg nephrilin IM3N1; group N1V=burn+2 mg/kg IM3N1vlp; group N1D=burn+2 mg/kg IM3N1dec; group N1F=burn+2 mg/kg IM3N1fen; group N1I=burn+2 mg/kg IM3N1ibu. The first dose was administered after completion of the scald procedure. Injection volume was 400 uL.

nephrilin IM3N1 peptide has previously been shown to protect rats from loss of lean body mass, kidney function and glycemic control, complications that endure in burn patient populations. Nephrilin's mechanism of action appears to involve protection from excessive oxidative stress. Using quantitative reverse transcriptase polymerase chain reaction (qRT-PCR) amplification of transcripts in total RNA extracted from dorsal root ganglia (DRG) of male rats 14 days after exposure to thermal insult, we query the relative levels of expression of 34 genes believed to be associated with oxidative stress biology in the CNS. We use these data to explore the central role of oxidative stress in astrogliosis, immunosuppression and mitochondrial homeostasis. This subset analysis of DRG from a previously published study (n=3 per group) is associated with the following effects in the study (Table x7A):

TABLE x7A

|  | SHAM | BURN + VEHICLE | BURN + IM3N1 |
|---|---|---|---|
| Lean Body Mass (DEXA) | 343.6 ± 15.7* | 304.9 ± 9.2 | 328.5 ± 5.1* |
| Glycemic Control (GTT AUC mg · dL · hr) | 44.7 ± 19.0** | 117.0 ± 19.1 | 69.0 ± 18.1* |
| Kidney Function (eGFR, calculated) | 1.21 ± 0.23* | 0.58 ± 0.18 | 1.29 ± 0.32* |
| Urinary 8-isoprostate (ng/pg cystatin) | 5.02 ± 2.91** | 26.44 ± 1.60 | 4.53 ± 1.21** |

The Table below shows the primers used in the RT-PCR. Rats that received nephrilin IM3N1 treatment (4 mg/kg by subcutaneous bolus injection once daily for seven days after scald injury) showed significantly reduced elevations in gene expression of key genes. In this study, using quantitative reverse transcriptase polymerase chain reaction (qRT-PCR) amplification of transcripts in total RNA extracted from dorsal root ganglia of male rats 14 days after exposure to thermal insult, the relative levels of expression of 34 genes believed to be associated with oxidative stress biology in the CNS were queried, with an emphasis on astrogliosis, immunosuppression and mitochondrial homeostasis. The 34 genes studied were selected based on their known implication in the above processes, as described in the scientific literature. Dorsal root ganglia (DRG) were dissected from male adult Sprague Dawley rats (300 gm, Charles River Laboratories, Wilmington, MA, USA), three randomly selected animals in each treatment group were used (Group 1:sham; Group 2: burn+vehicle; Group 3: burn+IM3N1) and total RNA was extracted from each pool using the Rneasy Midi Kit (Qiagen, Germantown, MD). Yield was ~30 ug RNA per pool and A260/A280 ratios were between 1.87-2.04 in all cases. The high quality of each RNA prep was further confirmed by electrophoresis (using Eukaryote Total RNA Nano). For quantitative reverse transcriptase polymerase chain reaction (qRT-PCR) RNAs were diluted in RNase/DNase free water and aliquoted into wells in triplicate. Approximately 100 ng of RNA was used per well. A one step qPCR method was performed using Luna Universal One-Step RT-qPCR kit (New England Biolabs, Ipswich, MA) containing reverse transcriptase enzyme mix. Primer pairs for each gene were synthesized for the SYBR assay. The following standard qPCR cycling conditions were used: 55C for 10' (for RT), 95C for 1' followed by 40 cycles at 95C for 10 s. 58C for 30 s. Background was set at 3-10 cycles and the threshold was set at 0.02 for all runs. Ct values were collected and analyzed using the "delta-delta Ct" method. Transcript data for each gene are shown relative to GAPDH, a house-keeping gene. Sham group value was set to 1. Gene groups: [A] astrocyte activation; [B] MDSC-mediated immunosuppression; [C] Mitochondrial homeostasis; [D] Downstream effects of oxidative stress;

|  | Group 1 Mean | SD | p vs gp2 | Group 2 Mean | SD | Group 3 Mean | SD | p vs gp2 |
|---|---|---|---|---|---|---|---|---|
| [A] |  |  |  |  |  |  |  |  |
| GFAP | 1.03 | 0.05 | 0.0073 | 6.08 | 0.76 | 2.40 | 0.38 | 0.0052 |
| CTGF | 0.94 | 0.09 | 0.0062 | 3.14 | 0.36 | 1.61 | 0.16 | 0.0086 |
| AQP4 | 1.06 | 0.09 | 0.0106 | 9.18 | 1.47 | 0.59 | 0.12 | 0.0093 |
| Pi16 | 1.10 | 0.11 | 0.0004 | 7.90 | 0.36 | 2.40 | 0.12 | 0.0005 |
| GALANIN | 0.98 | 0.07 | 0.0078 | 31.73 | 4.72 | 18.50 | 2.14 | 0.0250 |
| NPY | 1.02 | 0.07 | 0.0068 | 47.46 | 6.66 | 29.50 | 3.67 | 0.0245 |
| S100A9 | 1.00 | 0.07 | 0.0132 | 8.85 | 1.58 | 5.01 | 0.56 | 0.0401 |
| [B] |  |  |  |  |  |  |  |  |
| SLC7A11 | 1.02 | 0.09 | 0.0045 | 3.41 | 0.35 | 4.78 | 0.41 | NS |
| NRF2 | 1.00 | 0.06 | 0.0138 | 1.27 | 0.09 | 1.29 | 0.12 | NS |
| ARG1 | 0.99 | 0.04 | 0.0000 | 3.01 | 0.08 | 3.09 | 0.38 | NS |
| CD63 | 1.07 | 0.06 | 0.0309 | 1.95 | 0.29 | 1.88 | 0.19 | NS |
| CCL2 | 0.95 | 0.07 | 0.0006 | 2.62 | 0.04 | 3.17 | 0.23 | NS |
| [C] |  |  |  |  |  |  |  |  |
| TFAM | 1.09 | 0.12 | 0.0017 | 1.81 | 0.09 | 1.14 | 0.06 | 0.0011 |
| UCP2 | 1.09 | 0.08 | 0.0130 | 1.73 | 0.18 | 1.22 | 0.05 | 0.0295 |
| BOK | 0.97 | 0.05 | 0.0048 | 1.92 | 0.15 | 1.10 | 0.07 | 0.0041 |
| RAC1 | 1.05 | 0.06 | 0.0034 | 1.66 | 0.06 | 1.00 | 0.15 | 0.0088 |
| NOX2 | 1.10 | 0.11 | 0.0002 | 2.59 | 0.06 | 2.07 | 0.09 | 0.0017 |
| NOX4 | 0.97 | 0.04 | 0.0031 | 6.53 | 0.55 | 6.57 | 0.49 | NS |
| OXR1 | 0.98 | 0.12 | 0.6475 | 1.02 | 0.21 | 1.04 | 0.10 | NS |
| HCRTR1 | 1.09 | 0.10 | 0.0343 | 3.20 | 0.72 | 1.42 | 0.19 | 0.0423 |
| SHC1 | 1.10 | 0.13 | 0.0053 | 1.82 | 0.05 | 2.34 | 0.23 | NS |
| GLUL | 1.06 | 0.04 | 0.0018 | 1.64 | 0.07 | 1.53 | 0.06 | NS |
| SLC23A2 | 1.08 | 0.14 | 0.0356 | 1.43 | 0.13 | 1.47 | 0.13 | NS |
| STEAP4 | 1.06 | 0.09 | 0.0032 | 1.53 | 0.05 | 1.77 | 0.23 | NS |
| PINK1 | 1.02 | 0.14 | 0.0474 | 1.47 | 0.02 | 1.35 | 0.02 | NS |
| MFN2 | 1.02 | 0.11 | 0.0138 | 1.54 | 0.14 | 1.48 | 0.11 | NS |
| FIS1 | 0.98 | 0.04 | 0.1934 | 0.93 | 0.03 | 0.90 | 0.14 | NS |
| PPARGC1A | 1.03 | 0.16 | 0.8383 | 1.13 | 0.22 | 1.00 | 0.09 | NS |
| ACMSD | 0.98 | 0.03 | 0.6012 | 0.95 | 0.09 | 0.97 | 0.12 | NS |

-continued

|  | Group 1 Mean | SD | p vs gp2 | Group 2 Mean | SD | Group 3 Mean | SD | p vs gp2 |
|---|---|---|---|---|---|---|---|---|
| [D] | | | | | | | | |
| PLSCR1 | 1.01 | 0.12 | 0.0007 | 2.27 | 0.16 | 2.30 | 0.32 | NS |
| BACE1 | 0.99 | 0.08 | 0.0004 | 1.75 | 0.10 | 1.42 | 0.15 | NS |
| SLC12A5 | 1.00 | 0.07 | 0.0354 | 1.74 | 0.27 | 1.38 | 0.15 | NS |
| SLC12A2 | 1.03 | 0.14 | 0.0484 | 1.37 | 0.02 | 1.59 | 0.15 | NS |

Example 8. Post-Burn Wound Healing Study with Peptide IM3vlp

Experiment x8A. Male rats treated with 4 mg/kg nephrilin peptide IM3N1 for 2 weeks in Example 5 were subsequently treated 3× weekly (Mon-Wed-Fri) for 4 weeks with vehicle (n=12) or with 1 mg/kg IM3vlp peptide (n=12) by subcutaneous bolus injection (200 uL volume). Longitudinal wound length between the hairlines was measured at 6 weeks, and this value was corrected for nose-to-ear length and width of each animal. The mean resulting value (in arbitrary units) is shown below. Wound length is reduced by one-third by treating with IM3vlp from weeks 2-6. * $p<0.05$, ** $p<0.01$ IM3vlp vs vehicle

| Burn Group (n = 4) | Weeks 2-6 (vehicle) | Weeks 2-6 (1 mg/kg IM3vlp) |
|---|---|---|
| Vehicle | 127.1 ± 22.0 | 89.7 ± 17.7* |
| Nephrilin IM3N1 | 131.3 ± 18.6 | 92.4 ± 19.5* |
| Nephrilin IM3N1 + zinc | 121.7 ± 24.8 | 83.2 ± 15.4* |
| Nephrilin IM3N1 + iron | 115.9 ± 5.7 | 72.6 ± 12.8** |

Example 9. Iron and Calcium Stimulate the Binding of PI(4,5)P2 to Immodulator Peptides Polyphosphoinositides (PPI) and in particular PI(4,5)P2, are among the most highly charged molecules in cell membranes, are important in many cellular signaling pathways.

Experiment x9A

Immodulator peptides IM1, IM3 and IM5 (400 ng/well) in PBS were bound to streptavidin-coated 96-well plates at room temperature for 60 minutes, in the presence or absence of 500 uM calcium chloride. Each well also received 200 ng cold PPI plus 10 ng FITC-labeled PI(4,5)P2 or PI(4)P1. The tables below show the relative fluorescence (with/without calcium background) expressed as a percentage of the highest binder, FITC-PI(4,5)P2+cold PI(3,5)P2, which was 2,496 fluorescence units. Background binding without calcium was, in all cases, 200-300 fluorescence units. The results show that IM3 is the only one of the 3 peptides to bind PI(4,5)P2—but not (PI(4)P1—in a calcium-dependent manner. Excess PPI biphosphates (but not triphosphate, or any of the monophosphates) dramatically stimulated binding, especially PI(3,5)P2. This synergy was as expected (see above).

| | IM1 | | | IM3 | | | IM5 | | |
|---|---|---|---|---|---|---|---|---|---|
| cold PPI | Mean | SD | P value | Mean | SD | P value | Mean | SD | P value |
| FITC-PI(4,5)P | | | | | | | | | |
| None | 1.6 | 1.5 | NS | 2.2 | 2.7 | NS | 2.6 | 3.5 | NS |
| 3-P1 | 3.1 | 3.0 | NS | 1.7 | 0.2 | NS | 0.3 | 3.5 | NS |
| 4-P1 | 1.3 | 2.7 | NS | 6.3 | 3.2 | NS | 2.3 | 0.9 | NS |
| 5-P1 | 0.5 | 2.9 | NS | 10.4 | 2.9 | NS | 2.7 | 1.2 | NS |
| 3,4-P2 | 1.1 | 3.7 | NS | 51.5 | 7.6 | 0.0450 | 12.3 | 8.1 | NS |
| 4,5-P2 | 0.8 | 1.8 | NS | 63.7 | 7.7 | 0.0356 | 7.6 | 8.5 | NS |
| 3,5-P2 | 4.3 | 2.1 | NS | 100.0 | 1.0 | 0.0052 | 16.9 | 11.5 | NS |
| 3,4,5-P3 | 0.1 | 2.2 | NS | 3.2 | 0.5 | NS | 0.2 | 1.4 | NS |
| FITC-PI(4)P1 | | | | | | | | | |
| None | 1.6 | 1.5 | NS | 2.5 | 2.9 | NS | 2.1 | 1.2 | NS |
| 3-P1 | 3.1 | 3.0 | NS | 2.5 | 0.3 | NS | 0.9 | 2.9 | NS |
| 4-P1 | 2.7 | 3.0 | NS | 2.4 | 0.7 | NS | 0.8 | 2.4 | NS |
| 5-P1 | 0.5 | 2.9 | NS | 1.9 | 1.4 | NS | 0.4 | 1.7 | NS |
| 3,4-P2 | 2.6 | 1.5 | NS | 2.4 | 0.6 | NS | 1.7 | 0.0 | NS |
| 4,5-P2 | 0.8 | 1.8 | NS | 0.1 | 0.5 | NS | 1.8 | 1.5 | NS |
| 3,5-P2 | 4.3 | 2.1 | NS | 5.6 | 0.9 | NS | 1.3 | 1.9 | NS |
| 3,4,5-P3 | 0.1 | 2.2 | NS | 1.2 | 0.5 | NS | 1.2 | 1.0 | NS |

The binding of PPIs by immodulator peptides (or the IGFBP proteins from which their sequences were derived) has never previously been shown.

Experiment x9B

Binding of immodulator peptides to Echelon PPI Arrays. PPI arrays were purchased from Echelon Biosciences (Sal Lake City, UT) and used according to the manufacturer's recommendations. Colorimetric readout from each 100 pmol PPI spot in the array is expressed as 0=no binding, 1=low binding, 2=medium binding and 3=high binding. The results are shown below. The results show binding of IM3 and IM5 (and, to a lesser extent, IM6) to PI(4,5)P2 but not phospho-inositol or PI(4)P1, except that IM5 does show some binding to PI(4)P1. In addition, IM3 and IM5 show slight binding to PI(3,4,5)P3.

|            | IM1 | IM2 | IM3 | IM4 | IM5 | IM6 |
|------------|-----|-----|-----|-----|-----|-----|
| PI         | 0   | 0   | 0   | 0   | 0   | 0   |
| PI(4)P1    | 0   | 0   | 0   | 0   | 2   | 0   |
| PI(4,5)P2  | 0   | 0   | 3   | 0   | 3   | 1   |
| PI(3,4,5)P3| 0   | 0   | 1   | 0   | 1   | 0   |

Experiment x9C

NTA-coated 96-well plates were charged with either 500 uM zinc chloride or 500 uM ferric chloride and washed. Immodulator peptide IM3 (100 ng/well) and FITC-PI(4,5)P2 (50 ng/well) were added, with or without 2 ug/well cold PPI, and incubated at room temperature for 60 minutes. The plate was washed and counted in a fluorometer. The results are shown below. The results show that NTA-bound iron can bind IM3 peptide, and binding is enhanced by PI(3,5)P2 but not by PI(3)P1. *p<001 versus no metal control; #p<0.01 versus ferric iron alone.

| Metal       | Cold PPI  | Mean ± SD    |
|-------------|-----------|--------------|
| No metal    | None      | 0.0 ± 0.2    |
| Zinc        | None      | 2.2 ± 0.3*#  |
| Ferric iron | None      | 80.1 ± 1.8*  |
| Ferric iron | PI(3)P1   | 78.5 ± 5.8*  |
| Ferric iron | PI(3,5)P2 | 100.0 ± 3.2*#|

Experiment x9D

To a streptavidin-coated 96-well plate, 400 ng peptide IM3 or IM5 were bound per well. Each well received 100 uL of sodium acetate buffer pH5.2 containing 500 uM EDTA, Calcium Chloride, Zinc Chloride or Ferric Chloride. Each well additionally contained 50 ng FITC-PI(4,5)P2 plus 2 ug of either cold PI(3,4)P2, PI(4,5)P2, PI(3,5)P2 or buffer. All assays were done in sextuplicate. After incubation at room temperature for 60 mins, wells were washed and counted in a fluorometer set at FITC excitation/emmission wavelengths. The results are shown below. At low pH conditions of this experiment, cold PPI did not enhance binding of immodulator peptide to PI(4,5)P2 as much in the presence of calcium, but did so dramatically in the presence of ferric iron.

| IM3 peptide:  | EDTA    | Calcium    | Zinc        | Ferric Iron    |
|---------------|---------|------------|-------------|----------------|
| Buffer        | 30 ± 22 | 142 ± 29*  | 138 ± 388*  | 772 ± 168*#    |
| Cold PI(3,4)P2| 26 ± 25 | 48 ± 61    | 65 ± 16     | 2,162 ± 269*#  |
| Cold PI(4,5)P2| 10 ± 16 | 32 ± 23    | 21 ± 22     | 1,464 ± 320*#  |
| Cold PI(3,5)P2| 63 ± 26 | 88 ± 22    | 118 ± 43    | 2,036 ± 303*#  |

*$p < 0.001$ vs buffer control;
$p < 0.001$ vs ferric iron

| IM5 peptide:  | EDTA     | Calcium    | Zinc        | Ferric Iron    |
|---------------|----------|------------|-------------|----------------|
| Buffer        | 88 ± 23  | 234 ± 34*  | 236 ± 55*   | 1,111 ± 167*#  |
| Cold PI(3,4)P2| 150 ± 81 | 205 ± 50   | 151 ± 51    | 2,150 ± 420*#  |
| Cold PI(4,5)P2| 81 ± 95  | 163 ± 80   | 104 ± 21    | 1,447 ± 304*#  |
| Cold PI(3,5)P2| 205 ± 71 | 489 ± 146* | 353 ± 29*   | 2,026 ± 176*#  |

*$p < 0.001$ vs EDTA control;
$p < 0.001$ vs calcium and zinc

Example 10. Anti-Cancer Immodulator Peptides

Immune modulation functions of immodulator peptides have great potential untility in the field of cancer. A375 cell line was obtained from American Type Culture Collection (ATCC). They were grown in a T-75 flask in DMEM Medium containing 10% fetal bovine serum and penicillin-streptomycin at 37° C. in a humidified, 5% CO2 incubator. Cells (100 ml, 2,000 cells/well) were plated in a 96-well plate and incubated overnight at 37° C. in a humidified, 5% CO2 incubator. Next day, 10 ml/well of compounds were added (quadruplicate wells). After 72 hour incubation with the compound, cell viability was measured in a luminometer after the addition of 100 mL/well CellTiterGlo reagent (Promega Inc, Madison, WI) as recommended by the manufacturer.

Experiment x10A. Anti-cancer activity of immodulator peptides on A375 cells. A 96-well plate was seeded with 2,000 A375 cells per well in DMEM medium containing 10% FBS and PenStrep. After 24 hrs at 37 deg C., compounds and peptides were added (each treatment done in quadruplicate). After a further 72 hours incubation, 100 uL/well of CTG assay reagent purchased from Promega Inc. (Madison, WI) was added. Plate was read after 10 minutes, as recommended by the manufacturer. Peptides were added at 2 uM. The results of this experiment are shown below, expressed as percent survival of A375 cells. They show that anti-melanoma activity of various immodulator peptides are influenced by the core immodulator sequence, extension sequences, N-terminally conjugated carboxylic acids, and RIG-I co-inducer (4 uM). *$p<0.05$, **$p<0.01$ vs "no peptide" control; Kin1400=4 uM (RIG-I agonist); vlp=valproic; dec=decanoic; lau=lauric; rg108=RG108; h4p=h4-pentynoic; bpa=bromopyruvic; nd=not determined.

| Peptide | Sequence | Buffer | Kin1400 | |
|---|---|---|---|---|
| | No peptide | 100 | 100.7 | |
| IM1 | KNGFYHSRQCETSMDGEAGLCW | 102.1 | nd | SEQ ID NO: 15 |
| IM2 | KHGLYNLKQCKMSLNGQRGECW | 99.0 | nd | SEQ ID NO: 16 |
| IM3 | KKGFYKKKQCRPSKGRKRGFCW | 100.3 | 62.2** | SEQ ID NO: 17 |
| IM4 | RNGNFHPKQCHPALDGQRGKCW | 98.8 | nd | SEQ ID NO: 18 |
| IM5 | RKGFYKRKQCKPSRGRKRGICW | 103.4 | nd | SEQ ID NO: 19 |
| IM6 | HRGFYRKRQCRSSQGQRRGPCW | 102.2 | Nd | SEQ ID NO: 20 |
| IM3avd | KKGFYKKKQCRPSKGRKRGFCWAVD | 96.0 | 12.5** | SEQ ID NO: 23 |
| IM3fvs | KKGFYKKKQCRPSKGRKRGFCWFVS | 96.1 | 22.6** | SEQ ID NO: 25 |
| IM3vlp | (vlp)-KKGFYKKKQCRPSKGRKRGFCW | 93.9** | 32.6** | SEQ ID NO: 17 |
| IM3dec | (dec)-KKGFYKKKQCRPSKGRKRGFCW | 89.0** | 53.8** | SEQ ID NO: 17 |
| IM3lau | (lau)-KKGFYKKKQCRPSKGRKRGFCW | 96.6* | 17.4** | SEQ ID NO: 17 |
| IM3rg8 | (rg108)-KKGFYKKKQCRPSKGRKRGFCW | 89.9** | 105.8 | SEQ ID NO: 17 |
| IM3h4p | (h4p)-KKGFYKKKQCRPSKGRKRGFCW | 91.7** | Nd | SEQ ID NO: 17 |
| IM3K1 | SLNPEWNETKGFYKKKQCRPSKGRKRGFCW | 92.5** | 17.0** | SEQ ID NO: 26 |
| IM3K1bpa | (bpa)SLNPEWNETKGFYKKKQCRPSKGRKRGFCW | 98.4 | Nd | SEQ ID NO: 26 |
| IM3K1.11 | SLNPEWNETKKGFYKKKQCRPSKGRKRGFCW | 95.3* | Nd | SEQ ID NO: 27 |
| IM2K1 | SLNPEWNETHGLYNLKQCKMSLNGQRGECW | 96.2 | Nd | SEQ ID NO: 28 |

Example 11. Collagen Stimulating Activity of Immodulator Peptides

Immune modulation functions of immodulator peptides have potential untility in the field of cosmetics. HFF-1 cell line was obtained from American Type Culture Collection (ATCC). Cells were grown in a T-75 flask in DMEM Medium containing 10% fetal bovine serum and penicillin-streptomycin at 37° C. in a humidified, 5% CO2 incubator. Cells (100 ml, 2,000 cells/well) were plated in a 96-well plate and incubated overnight at 37° C. in a humidified, 5% CO2 incubator. Next day, 10 ml/well of compounds were added (quadruplicate wells). After 72 hour incubation with the compound, supernatants were collected for Collagen-1 ELISA assay and cell viability was measured in a luminometer after the addition of 100 mL/well CellTiterGlo reagent (Promega Inc, Madison, WI) as recommended by the manufacturer.

| Peptide | Sequence | COL1 | |
|---|---|---|---|
| | No peptide | 100 | |
| IM1 | KNGFYHSRQCETSMDGEAGLCW | 98 | SEQ ID NO: 15 |
| IM2 | KHGLYNLKQCKMSLNGQRGECW | 109 | SEQ ID NO: 16 |
| IM3 | KKGFYKKKQCRPSKGRKRGFCW | 101 | SEQ ID NO: 17 |
| IM4 | RNGNFHPKQCHPALDGQRGKCW | 105 | SEQ ID NO: 18 |
| IM5 | RKGFYKRKQCKPSRGRKRGICW | 93 | SEQ ID NO: 19 |
| IM6 | HRGFYRKRQCRSSQGQRRGPCW | 112 | SEQ ID NO: 20 |
| IM3bex | (bex)-KKGFYKKKQCRPSKGRKRGFCW | 102 | SEQ ID NO: 17 |
| IM3isf | (isf)-KKGFYKKKQCRPSKGRKRGFCW | 131* | SEQ ID NO: 17 |
| IM3vlp | (vlp)-KKGFYKKKQCRPSKGRKRGFCW | 157** | SEQ ID NO: 17 |
| IM3dec | (dec)-KKGFYKKKQCRPSKGRKRGFCW | 114 | SEQ ID NO: 17 |
| IM3cin | (cin)-KKGFYKKKQCRPSKGRKRGFCW | 106 | SEQ ID NO: 17 |
| IM3rhn | (rhn)-KKGFYKKKQCRPSKGRKRGFCW | 68** | SEQ ID NO: 17 |

-continued

| Peptide | Sequence | COL1 | |
|---|---|---|---|
| IM3K9 | AFNSYELGSKGFYKKKQCRPSKGRKRGFCW | 155** | SEQ ID NO: 29 |
| IM3K9.1 | AFNSYELGSKKGFYKKKQCRPSKGRKRGFCW | 156** | SEQ ID NO: 30 |
| IM3K9c | AFNSYELGSKGFYKKKQCRPSKGRKRGFCWAVDKY | 158** | SEQ ID NO: 31 |
| IM3K8 | FNSYELGSLKKGFYKKKQCRPSKGRKRGFCW | 98 | SEQ ID NO: 32 |

Experiment x11A

Collagen stimulating activity of immodulator peptides in HFF-1 dermal fibroblasts. Peptides were added to cells at 2 uM. COL1 immunoreactivity was measured in the supernatants of cultured cells by ELISA using a rabbit monoclonal anti-COL1 primary antibody (Abcam, Cambridge, MA). The results of this experiment are shown in Table above. Control (buffer) value of immunoreactivity was set to 100. The data show that collagen stimulating activity of various immodulator peptides are influenced by specific extension sequences and by N-terminally conjugated carboxylic acids. *$p<0.05$, **$p<0.01$ vs "no peptide" control; bex=bexarotene; isf=isoferulic; vlp=valproic; dec=decanoic; cin=cinnamic; rhn=rhein;

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A modified synthetic peptide, 20-60 amino acids in length, comprising:
   (i) an amino acid sequence corresponding to SEQ ID NO:1 or SEQ ID NO:2; and
   (ii) a small molecule of molecular mass less than one thousand daltons linked covalently to the amino terminus of the amino acid sequence;
   wherein said small molecule is selected from the group consisting of: decanoic acid, lignoceric acid, adapalene, bexarotene, trans-cinnamic acid, fenofibric acid, valproic acid, 2-hexyl-4-pentynoic acid and ibuprofen.

2. The modified peptide according to claim 1, wherein the amino acid sequence is carboxyterminally extended by the amino acid sequence ZV, wherein Z is any amino acid except L-cysteine or L-alanine.

3. The modified peptide according to claim 1, wherein the amino acid sequence consists of SEQ ID NO:5.

4. The modified peptide according to claim 1, wherein the amino acid sequence consists of SEQ ID NO:7.

5. The modified peptide according to claim 1, further comprising an amino acid sequence selected from the group consisting of: SEQ ID NOs:9-14.

6. The modified peptide according to claim 1, wherein the modified peptide is complexed with a metal selected from the group consisting of: ferrous iron, ferric iron, zinc, copper, vanadium, ruthenium, cobalt, titanium, manganese, and calcium.

7. The modified peptide according to claim 1, wherein the modified peptide is complexed with a glycosaminoglycan selected from the group consisting of: heparin, heparan sulfate, chondroitin sulfate, keratan sulfate, dermatan sulfate, and hyaluronate.

* * * * *